(12) United States Patent  
Miao et al.

(10) Patent No.: US 12,600,782 B2  
(45) Date of Patent: Apr. 14, 2026

(54) ANTI-PD-L1 AND PD-L2 ANTIBODY AND DERIVATIVES AND USE THEREOF

(71) Applicant: BIOTHEUS INC., Zhuhai (CN)

(72) Inventors: Xiaoniu Miao, Zhuhai (CN); Fan Wu, Zhuhai (CN); Cheng Chen, Zhuhai (CN)

(73) Assignee: BIOTHEUS INC., Zhuhai (CN)

( * ) Notice: Subject to any disclaimer, the term of this patent is extended or adjusted under 35 U.S.C. 154(b) by 791 days.

(21) Appl. No.: 17/995,197

(22) PCT Filed: Mar. 30, 2021

(86) PCT No.: PCT/CN2021/084196  
§ 371 (c)(1),  
(2) Date: Sep. 30, 2022

(87) PCT Pub. No.: WO2021/197358  
PCT Pub. Date: Oct. 7, 2021

(65) Prior Publication Data  
US 2023/0203167 A1 Jun. 29, 2023

(30) Foreign Application Priority Data

Mar. 31, 2020 (CN) .......................... 202010246560.0

(51) Int. Cl.  
| | |
|---|---|
| *C07K 16/28* | (2006.01) |
| *A61K 47/68* | (2017.01) |
| *A61P 35/00* | (2006.01) |
| *G01N 33/574* | (2006.01) |

(52) U.S. Cl.  
CPC ...... *C07K 16/2827* (2013.01); *A61K 47/6849* (2017.08); *A61P 35/00* (2018.01); *G01N 33/57492* (2013.01); *C07K 2317/24* (2013.01); *C07K 2317/31* (2013.01); *C07K 2317/522* (2013.01); *C07K 2317/565* (2013.01); *C07K 2317/569* (2013.01); *C07K 2317/76* (2013.01); *C07K 2317/92* (2013.01); *G01N 2333/70532* (2013.01)

(58) Field of Classification Search  
None  
See application file for complete search history.

(56) References Cited

U.S. PATENT DOCUMENTS

2015/0156673 A1* 6/2015 Kuwahara ......... H04W 28/0205  
370/329  
2025/0011402 A1* 1/2025 Abnousi ............ C07K 16/1282

FOREIGN PATENT DOCUMENTS

| | | | |
|---|---|---|---|
| CN | 107686520 A | 2/2018 | |
| CN | 109096396 A | 12/2018 | |
| CN | 110003333 A | 7/2019 | |
| CN | 110256564 A | 9/2019 | |
| CN | 110372793 A | 10/2019 | |
| CN | 107636013 B | 12/2019 | |
| CN | 110627906 A | 12/2019 | |
| JP | 2014042515 A * | 3/2014 | |
| JP | 2015527342 A | 9/2015 | |
| WO | WO-0171042 A2 * | 9/2001 | ........... C12Q 1/6876 |
| WO | WO-2008077945 A2 * | 7/2008 | ............. C07K 16/24 |
| WO | WO-2009068625 A2 * | 6/2009 | ............. A61P 37/02 |
| WO | WO-2009147248 A2 * | 12/2009 | ........ C07K 16/1027 |
| WO | WO-2013110531 A1 * | 8/2013 | ........ C07K 16/2863 |
| WO | 2014022758 A1 | 2/2014 | |
| WO | WO-2016125089 A1 * | 8/2016 | ............. A61P 43/00 |
| WO | WO-2018077893 A1 * | 5/2018 | ............. A61P 37/02 |
| WO | WO-2018220235 A1 * | 12/2018 | ............. A61P 19/00 |
| WO | WO-2019096121 A1 * | 5/2019 | ............. A61P 35/00 |
| WO | 2019149219 A1 | 8/2019 | |
| WO | 2019152979 A1 | 8/2019 | |
| WO | 2019191519 A1 | 10/2019 | |
| WO | WO-2021095031 A2 * | 5/2021 | ............. C07K 16/18 |
| WO | WO-2023091609 A2 * | 5/2023 | ........... C07K 16/244 |

OTHER PUBLICATIONS

ACS. Cancer Risk and Prevention. webpage saved Mar. 21, 2025. (Year: 2025).*  
Merriam-Webster. Definition of "Prevent". webpage saved Apr. 24, 2025. (Year: 2025).*  
Estep, Patricia et al.; "High throughput solution-based measurement of antibody-antigen affinity and epitope pinning"; mAbs; vol. 5, Issue 2; Mar. 1, 2013; ISSN: 1942-0862(Print) 1942-0870(Online); pp. 270-278.  
Vincke, Cecile et al.; "General Strategy to Humanize a Camelid Single-domain Antibody and Identification of a Universal Humanized Nanobody Scaffold"; The Journal of Biological Chemistry; vol. 284, No. 5; Jan. 30, 2009; pp. 3273-3284.

* cited by examiner

*Primary Examiner* — Julie Wu  
*Assistant Examiner* — Amy M. Chattin  
(74) *Attorney, Agent, or Firm* — NKL Law; Bin Lu; Allen Xue

(57) ABSTRACT

A PD-L1 nano-antibody and a PD-L2 nano-antibody, and a bispecific antibody having both the PD-L1 nano-antibody and the PD-L2 nano-antibody are disclosed. The bispecific antibody can block PD-1/PD-L1 and PD-1/PD-L2 pathways at the same time. The bispecific antibody can reactivate T cells, enhance immune responses, and more effectively improve the inhibitory effect on tumor occurrence and development.

13 Claims, 7 Drawing Sheets  
Specification includes a Sequence Listing.

CHO-hPD-L2 cell binding

FIG. 3

CHO-PD-1/PDL1 cell blocking assay

| | Bi-201 | Bi-202 | Bi-203-204 | ATE | HZ-K-Yr-13&14-02-03 |
|---|---|---|---|---|---|
| EC50 | 22.85 | 11.53 | 12.35 | 6.310 | 5.166 |

CHO-PD-1/PDL2 cell blocking assay

| | Bi-201 | Bi-202 | Bi-203-204 | HZ-D-NA-96-01 |
|---|---|---|---|---|
| EC50 | 32.24 | 20.77 | 8.354 | 13.44 |

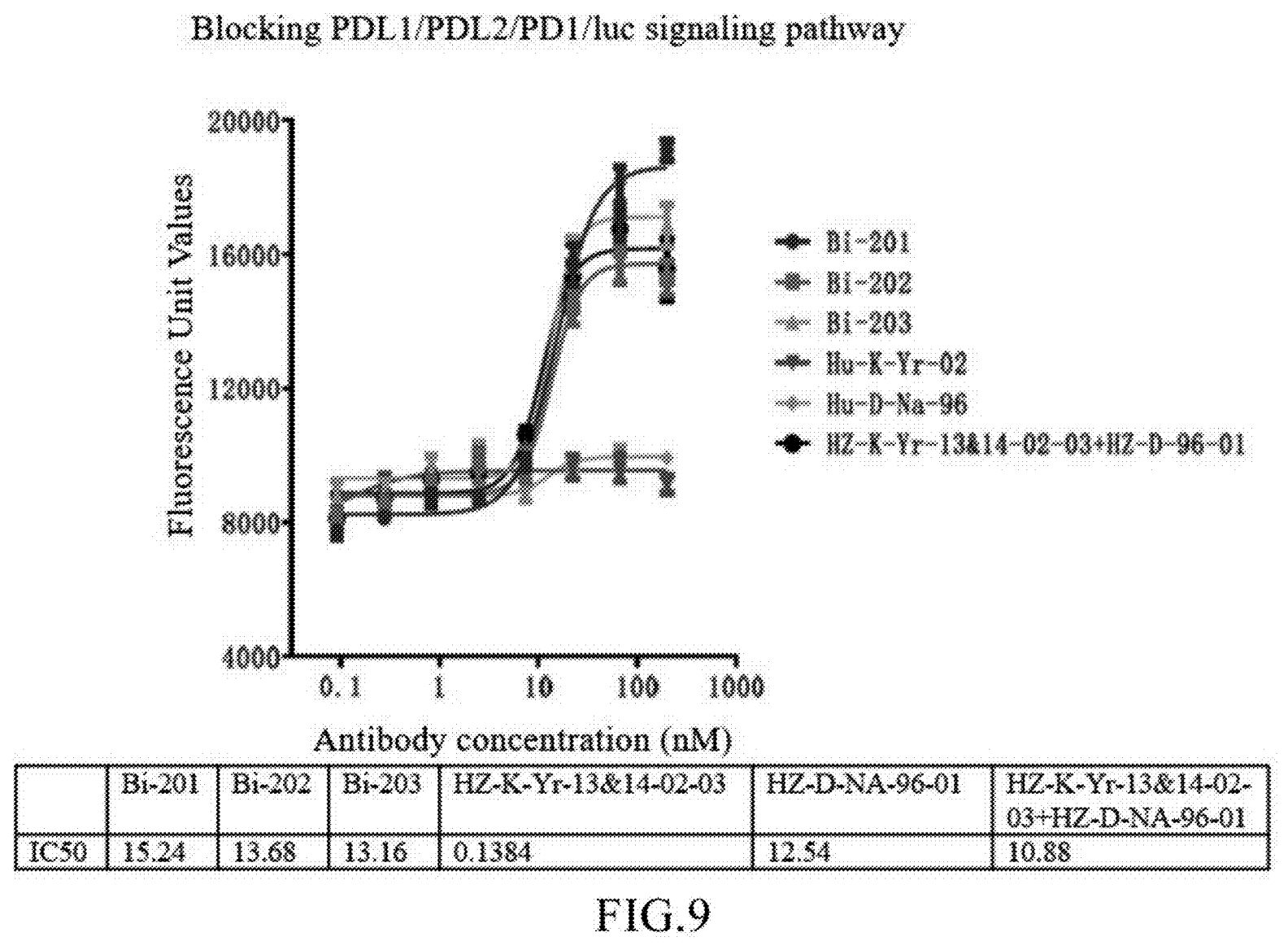

Blocking PDL1/PDL2/PD1/luc signaling pathway

| | Bi-201 | Bi-202 | Bi-203 | HZ-K-Yr-13&14-02-03 | HZ-D-NA-96-01 | HZ-K-Yr-13&14-02-03+HZ-D-NA-96-01 |
|---|---|---|---|---|---|---|
| IC50 | 15.24 | 13.68 | 13.16 | 0.1384 | 12.54 | 10.88 |

FIG.9

ANTI-PD-L1 AND PD-L2 ANTIBODY AND DERIVATIVES AND USE THEREOF

INCORPORATION OF SEQUENCE LISTING

This application contains a sequence listing submitted in Computer Readable Form (CRF). The CFR file containing the sequence listing entitled "PBA4085793 ST25.txt", which was created on Sep. 30, 2022, and is 72,875 bytes in size. The information in the sequence listing is incorporated herein by reference in its entirety.

TECHNICAL FIELD

The present invention relates to the technical field of biomedicine or biopharmaceuticals, in particular to an anti-PD-L1 and PD-L2 antibody and derivatives and use thereof.

BACKGROUND

Programmed death-1 (PD-1), also known as CD279, is a member of CD28 family. The cytoplasmic region of CD279 contains 2 tyrosine residues, one near the N-terminal is located in the immunoreceptor tyrosine-based inhibitory motif (ITIM), and the other one near the C-terminal is located in the immunoreceptor tyrosine-based switch motif (ITSM). PD-1 is mainly expressed on the surfaces of activated T lymphocytes, B lymphocytes and macrophages. Under normal circumstances, PD-1 can inhibit the function of T lymphocytes and promote the function of Treg, thus inhibiting autoimmune response and preventing the occurrence of autoimmune diseases.

Programmed death 1 ligand 1 (PD-L1), also known as CD274, is a member of the B7 family and is the ligand of PD-1. PD-L1 is a type I transmembrane protein consisting a total of 290 amino acids, including one IgV-like region, one IgC-like region, one transmembrane hydrophobic region and one intracellular region composed of 30 amino acids.

Different from other B7 family molecules, PD-L1 has a negative effect on regulating immune response. Studies have found that PD-L1 is mainly expressed in activated T cells, B cells, macrophages and dendritic cells. In addition to lymphocytes, PD-L1 is also expressed in endothelial cells of other tissues such as thymus, heart, placenta, etc., and various non-lymphatic systems such as melanoma, liver cancer, gastric cancer, renal cell cancer, ovarian cancer, colon cancer, breast cancer, esophageal cancer, head and neck cancer, etc. PD-L1 has certain universality in regulating autoreactive T. B cells and immune tolerance, and plays a role in peripheral tissue T and B cells response. High expression of PD-L1 on tumor cells is associated with poor prognosis in cancer patients.

However, in the occurrence of tumors, the PD-L1 expressed by tumor cells combined with PD-1 can promote tumor immune escape through inhibitory effect on lymphocytes. The combination of PD-L1 and PD-1 can lead to a variety of biological changes and immune regulation, such as inhibiting the proliferation and activation of lymphocytes, inhibiting the differentiation of CD4+ T cells into Th1 and Th17 cells, and inhibiting the release of inflammatory cytokines.

Programmed death 1 ligand 2 (PD-L2), also known as CD273 or B7-DC, is another important ligand of PD-1. The interaction between PD-1 and PD-L2 can inhibit the activation and proliferation of CD4+ T cells, reduce the release of cytokines, and increase the immune escape of tumor. Blocking the interaction between PD-1 and PD-L1 and PD-L2 at the same time can effectively liberate the inhibition of PD-1 pathway activation on immune system, activate the body's own immune system and kill tumors.

However, as of now, there is no bispecific single-domain antibody that simultaneously targets PD-L1/PD-L2 on the market. As an emerging force in the diagnosis and treatment of the new generation of antibodies, single-domain antibodies have the characteristics of high stability, good water solubility, simple humanization, high targeting, and strong penetration, and play a huge function beyond imagination in immune experiments, diagnosis and treatment.

Therefore, there is an urgent need in the art for a bispecific single domain antibody capable of simultaneously targeting PD-L1 and PD-L2.

SUMMARY OF THE INVENTION

The object of the present invention is to provide a bispecific antibody capable of simultaneously targeting PD-L1 and PD-L2.

In the first aspect of the present invention, it provides an anti-PD-L2 nanobody, and the complementarity determining regions (CDRs) of the VHH chain of the PD-L2 nanobody are composed of the following:

CDR1 with amino acid sequence as shown in SEQ ID NO: 57; CDR2 with amino acid sequence as shown in SEQ ID NO: 58; and CDR3 with amino acid sequence as shown in SEQ ID NO: 59; or CDR1 with amino acid sequence as shown in SEQ ID NO: 60; CDR2 with amino acid sequence as shown in SEQ ID NO: 61; and CDR3 with amino acid sequence as shown in SEQ ID NO: 62;

or, the amino acid sequence of the VHH chain of the anti-PD-L2 nanobody is as shown in SEQ ID NO: 1, 2, 4, 5, 6, 7, 8, 9, 10, 11, 13, 14, 17 or 18.

In another preferred embodiment, the CDR1, CDR2 and CDR3 are separated by the framework regions FR1, FR2, FR3 and FR4 of the VHH chain.

In another preferred embodiment, the amino acid sequence of the VHH chain of the anti-PD-L2 nanobody is as shown in SEQ ID NO: 3 (i.e., D-Na-96), 16 (i.e., HZ-D-Na-96-1), 12 (i.e., D-Ye-29) or 15 (i.e., HZ-D-Ye-29-3).

In another preferred embodiment, the anti-PD-L2 nanobody is humanized and the amino acid sequence of the VHH chain of the anti-PD-L2 nanobody is as shown in 16 (i.e., HZ-D-Na-96-1) or 15 (i.e., HZ-D-Ye-29-3).

In another preferred embodiment, the PD-L2 nanobody can block the interaction between PD-1 and PD-L2.

In the second aspect of the present invention, it provides an anti-PD-L1 nanobody, and the complementarity determining regions (CDRs) of the VHH chain of the PD-L1 nanobody are composed of the following:

CDR1 with amino acid sequence as shown in SEQ ID NO: 63; CDR2 with amino acid sequence as shown in SEQ ID NO: 64; and CDR3 with amino acid sequence as shown in SEQ ID NO: 65.

In another preferred embodiment, the CDR1, CDR2 and CDR3 are separated by the framework regions FR1, FR2, FR3 and FR4 of the VHH chain.

In another preferred embodiment, the amino acid sequence of the VHH chain of the anti-PD-L1 nanobody is as shown in SEQ ID NO: 19 (i.e., K-Yr-13&14-02), 20 (i.e., K-Yr-13&14-09), 21 (i.e., K-Yr-13&14-16) or 22 (i.e., HZ-K-Yr-13&14-02-3).

In another preferred embodiment, the anti-PD-L1 nanobody is humanized and the amino acid sequence of the VHH chain of the anti-PD-L1 nanobody is as shown in 22 (i.e., HZ-K-Yr-13&14-02-3).

In another preferred embodiment, the PD-L1 nanobody can block the interaction between PD-1 and PD-L1.

In the third aspect of the present invention, it provides a bispecific antibody, which comprises: the anti-PD-L1 nanobody of the second aspect of the present invention and the anti-PD-L2 nanobody of the first aspect of the present invention.

In another preferred embodiment, the bispecific antibody comprises 1-3 anti-PD-L1 nanobodies, preferably 1 or 2 anti-PD-L1 nanobodies.

In another preferred embodiment, the bispecific antibody comprises 1-3 anti-PD-L2 nanobodies, preferably 1 or 2 anti-PD-L2 nanobodies.

In another preferred embodiment, the bispecific antibody further comprises an Fc segment.

In another preferred embodiment, the Fc segment of the bispecific antibody is selected from the group consisting of a human IgG domain, a CH1+CL1 domain, and a combination thereof.

In another preferred embodiment, the human IgG domain is a modified mutant IgG domain, preferably a LALA mutant IgG domain.

In another preferred embodiment, the bispecific antibody contains a polypeptide with a structure as shown in Formula I or Formula II, or a polypeptide with a structure as shown in Formula III and Formula IV at the same time, $$A\text{-}L1\text{-}Fc1\text{-}L2\text{-}B \qquad \text{(Formula I)}$$

$$A\text{-}L3\text{-}B\text{-}L4\text{-}Fc1 \qquad \text{(Formula II)}$$

$$A\text{-}L5\text{-}Fc2\text{-}L6\text{-}Fc1 \qquad \text{(Formula III)}$$

$$B\text{-}L7\text{-}Fc2 \qquad \text{(Formula IV)}$$

wherein,

A and B are each independently an anti-PD-L1 nanobody as described in the second aspect of the present invention or an anti-PD-L2 nanobody as described in the first aspect of the present invention, and A and B are different antibodies;

L1, L2, L3 and L4 are each independently a peptide bond or a linker element;

both Fc1 and Fc2 are the Fc segment of the antibody, wherein Fc1 is the human IgG domain (preferably the LALA mutant IgG domain), and Fc2 is the CH1+CL domain;

"—" is a peptide bond.

In another preferred embodiment, the bispecific antibody has a polypeptide sequence of the structure as shown in Formula III and Formula IV, and the polypeptide of the structure as shown in Formula III and the polypeptide of the structure as shown in Formula IV form a heterodimer a through disulfide bonds.

In another preferred embodiment, the bispecific antibody has a polypeptide of the structure as shown in Formula I, and the polypeptide forms a homodimer i through disulfide bonding between Fc1.

In another preferred embodiment, the bispecific antibody has a polypeptide of the structure as shown in Formula II, and the polypeptide forms a homodimer ii through disulfide bonding between Fc1.

In another preferred embodiment, the bispecific antibody has a polypeptide sequence of the structure as shown in Formula III and Formula IV, and the polypeptide of the structure as shown in Formula III and the polypeptide of the structure as shown in Formula IV form a heterodimer a by disulfide bonding between Fc2, and the heterodimer ii forms a homodimer iii by disulfide bonding between Fc1.

In another preferred embodiment, the amino acid sequence of the PD-L1 nanobody is as shown in SEQ ID NO: 19, 20, 21 or 22, preferably SEQ ID NO: 22.

In another preferred embodiment, the bispecific antibody further comprises VHH chain of other anti-PD-L2 nanobody, and the amino acid sequence of the other PD-L2 nanobody is as shown in SEQ ID NO: 1, 2, 3, 4, 5, 6, 7, 8, 9, 10, 11, 12, 13, 14, 15, 16, 17 or 18.

In another preferred embodiment, the amino acid sequence of the VHH chain of anti-PD-L2 nanobody is as shown in SEQ ID NO: 3, 16, 12 or 15, preferably SEQ ID NO: 16 or 15.

In another preferred embodiment, the sequence of the linker elements is (4GS)n, wherein n is a positive integer (e.g., 1, 2, 3, 4, 5 or 6), preferably n=4.

In another preferred embodiment, the sequence of the linker elements is as shown in SEQ ID NO: 27, or has a sequence identity of ≥85% (preferably 90%, more preferably 95%) to the sequence shown in SEQ ID NO: 27.

In another preferred embodiment, the amino acid sequence of the LALA mutant human IgG domain is as shown in SEQ ID NO: 28, or has a sequence identity of ≥85% (preferably 90%, more preferably 95%) to the sequence shown in SEQ ID NO: 28.

In another preferred embodiment, the sequence of the CH1 domain is as shown in SEQ ID NO: 29, or has a sequence identity of ≥85% (preferably 90%, more preferably 95%) to the sequence shown in SEQ ID NO: 29.

In another preferred embodiment, the sequence of the CL domain is as shown in SEQ ID NO: 30, or has a sequence identity of ≥85% (preferably 90%, more preferably 95%) to the sequence shown in SEQ ID NO: 30.

In another preferred embodiment, the amino acid sequence of the bispecific antibody is as shown in SEQ ID NO: 23 or 24.

In another preferred embodiment, the bispecific antibody simultaneously contains a polypeptide of the structure shown in Formula III and Formula IV, wherein the amino acid sequence of the polypeptide of Formula III is shown in SEQ ID NO: 25, and the amino acid sequence of the polypeptide of Formula IV is shown in SEQ ID NO: 26.

In the fourth aspect of the present invention, it provides an isolated polynucleotide encoding the anti-PD-L2 nanobody of the first aspect of the present invention, the anti-PD-L1 nanobody of the second aspect of the present invention, or the bispecific antibody of the third aspect of the present invention.

In another preferred embodiment, the polynucleotide sequence is as shown in SEQ ID NO: 31, 32, 33, 34, 35, 36, 37, 38, 39, 40, 41, 42, 43, 44, 45, 46, 47 or 48.

In another preferred embodiment, the polynucleotide sequence is as shown in SEQ ID NO: 33 (i.e., D-Na-96), 46 (i.e., HZ-D-Na-96-1), 42 (i.e., D-Ye-29) or 45 (i.e., HZ-D-Ye-29-3), preferably SEQ ID NO: 46 or 45.

In another preferred embodiment, the polynucleotide sequence is as shown in SEQ ID NO: 49 (i.e., K-Yr-13&14-02), 50 (i.e., K-Yr-13&14-09), 51 (i.e., K-Yr-13&14-16) or 52 (i.e., HZ-K-Yr-13&14-02-3), preferably SEQ ID NO: 52.

In another preferred embodiment, the polynucleotide sequence is as shown in SEQ ID NO: 53 or 54.

In another preferred embodiment, the polynucleotide comprises a first polynucleotide with the sequence as shown in SEQ ID NO: 55, and a second polynucleotide with the sequence as shown in SEQ ID NO: 56.

In the fifth aspect of the present invention, it provides a vector comprising a polynucleotide of the fourth aspect of the present invention.

In another preferred embodiment, the vector is selected from the group consisting of DNA, RNA, a viral vector, a plasmid, a transposon, other gene transfer systems, and a combination thereof; preferably, the expression vector comprises a viral vector, such as a lentivirus, an adenovirus, an AAV virus, a retrovirus, and a combination thereof.

In the sixth aspect of the present invention, it provides a host cell comprising a vector of the fifth aspect of the present invention, or having the polynucleotide of the fourth aspect of the present invention integrated in the genome;

or, the host cell expresses the anti-PD-L2 nanobody of the first aspect of the present invention, the anti-PD-L1 nanobody of the second aspect of the present invention, or the bispecific antibody of the third aspect of the present invention.

In another preferred embodiment, the host cell comprises a prokaryotic cell or a eukaryotic cell.

In another preferred embodiment, the host cell is selected from the group consisting of *E. coli*, a yeast cell, and a mammalian cell.

In the seventh aspect of the present invention, it provides a method for producing anti-PD-L1 nanobodies, anti-PD-L2 nanobodies, or bispecific antibodies, comprising the steps:

(a) culturing the host cell of the sixth aspect of the present invention under suitable conditions to obtain a culture containing the anti-PD-L1 nanobodies, anti-PD-L2 nanobodies, or bispecific antibodies; and (b) purifying and/or isolating the culture obtained in step (a) to obtain the anti-PD-L1 nanobodies, anti-PD-L2 nanobodies, or bispecific antibodies.

In another preferred embodiment, the purification can obtain the target antibody by protein A affinity column purification and isolation.

In another preferred embodiment, the purity of the target antibody after purifying and isolating is greater than 95%, greater than 96%, greater than 97%, greater than 98%, greater than 99%, preferably 100%.

In the eighth aspect of the present invention, it provides an immune conjugate, which comprises:

(a) the anti-PD-L2 nanobody of the first aspect of the present invention, the anti-PD-L1 nanobody of the second aspect of the present invention, or the bispecific antibody of the third aspect of the present invention; and (b) a coupling moiety selected from the group consisting of a detectable label, a drug, a toxin, a cytokine, a radionuclide, or an enzyme, a gold nanoparticle/nanorod, a nanomagnetic particle, a viral coat protein or VLP, and a combination thereof.

In another preferred embodiment, the radionuclide comprises:

(i) a diagnostic isotope, which is selected from the group consisting of Tc-99m, Ga-68, F-18, I-123, I-125, I-131, In-111, Ga-67, Cu-64, Zr-89, C-11, Lu-177, Re-188, and a combination thereof; and/or (ii) a therapeutic isotope, which is selected from the group consisting of Lu-177, Y-90, Ac-225, As-211, Bi-212, Bi-213, Cs-137, Cr-51, Co-60, Dy-165, Er-169, Fm-255, Au-198, Ho-166, I-125, I-131, Ir-192, Fe-59, Pb-212, Mo-99, Pd-103, P-32, K-42, Re-186, Re-188, Sm-153, Ra223, Ru-106, Na24, Sr89, Tb-149, Th-227, Xe-133 Yb-169, Yb-177, and a combination thereof.

In another preferred embodiment, the coupling moiety is a drug or a toxin.

In another preferred embodiment, the drug is a cytotoxic drug.

In another preferred embodiment, the cytotoxic drug is selected from the group consisting of an anti-tubulin drug, a DNA minor groove binding agent, a DNA replication inhibitor, an alkylating agent, an antibiotic, a folate antagonist, an anti-metabolite, a chemotherapeutics sensitizer, a topoisomerase inhibitor, vinca alkaloid, and a combination thereof.

Examples of particularly useful cytotoxic drug classes comprises, for example, a DNA minor groove binding reagent, a DNA alkylation reagent, and a tubulin inhibitor, a typical cytotoxic drug includes, for example, auristatins, camptothecins, duocarmycins, etoposides, maytansines and maytansinoids (such as DM1 and DM4), taxanes, benzodiazepines or benzodiazepine containing drugs (e.g., pyrrolo [1,4]benzodiazepines (PBDs), indolinobenzodiazepines and oxazolidinobenzodiazepines), vinca alkaloids, and a combination thereof.

In another preferred embodiment, the toxin is selected from the group consisting of:

auristatins (e.g., auristatin E, auristatin F, MMAE and MMAF), chlortetracycline, maytansoids, ricin, ricin A-chain, combretastatin, docamicin, dolastatin, doxorubicin, daunorubicin, paclitaxel, cisplatin, cc1065, ethidium bromide, mitomycin, etoposide, tenoposide, vincristine, vinblastine, colchicine, dihydroxyanthraxdione, actinomycin, diphtheria toxin, *pseudomonas* exotoxin (PE) A, PE40, acacia toxin, acacia A chain, capsule root toxin A chain, α-octococcus, white tree Toxin, mitogellin, retstrictocin, phenomycin, enomycin, curicin, crotin, calicheamicin, *Sapaonaria officinalis* inhibitor, glucocorticoids, and a combination thereof.

In another preferred embodiment, the coupling moiety is a detectable label.

In another preferred embodiment, the conjugate is selected from: a fluorescent or luminescent label, a radioactive label, MRI (magnetic resonance imaging) or CT (electronic computer tomography) contrast agent, or an enzyme capable of producing detectable products, a radionuclide, a biological toxin, a cytokine (such as IL-2), an antibody, an antibody Fc fragment, an antibody scFv fragment, a gold nanoparticle/nanorod, a viral particle, a liposome, a nanomagnetic particle, a prodrug activating enzyme (such as DT-cardiomyolase (DTD) or biphenyl hydrolaselike protein (BPHL)), a chemotherapeutic agent (such as cisplatin).

In another preferred embodiment, the immunoconjugate comprises a multivalent (e.g., bivalent) anti-PD-L2 nanobody of the first aspect of the present invention, anti-PD-L1 nanobody of the second aspect of the present invention, or bispecific antibody of the third aspect of the present invention.

In another preferred embodiment, the multivalent refers to the amino acid sequence of the immunoconjugate comprises a plurality of replicates of the anti-PD-L2 nanobody of the first aspect of the present invention, the anti-PD-L1 nanobody of the second aspect of the present invention, or the bispecific antibody of the third aspect of the present invention.

In the ninth aspect of the present invention, it provides the use of the anti-PD-L2 nanobody of the first aspect of the present invention, the anti-PD-L1 nanobody of the second aspect of the present invention, or the bispecific antibody of the third aspect of the present invention, or the immuno-conjugate of the eighth aspect of the present invention, for the preparation of a medicament, a reagent, a test plate or a kit; wherein the reagent, the test plate or the kit is used to detect the PD-L1 and/or PD-L2 in the sample; wherein the medicament is used to treat or prevent tumors expressing PD-L1 (i.e., PD-L1 positive) or tumors expressing PD-L2.

In another preferred embodiment, the coupling moiety of the immunoconjugate is a diagnostic isotope.

In another preferred embodiment, the reagent is one or more reagents selected from the group consisting of an isotope tracer, a contrast agent, a flow detection reagent, a cellular immunofluorescence detection reagent, a magnetic nanoparticle and an imaging agent.

In another preferred embodiment, the reagent for detecting PD-L1 and/or PD-L2 in the sample is a contrast agent for detecting PD-L1 and/or PD-L2 molecules (in vivo).

In another preferred embodiment, the detection is an in vivo detection or an in vitro detection.

In another preferred embodiment, the detection comprises a flow cytometry detection and a cellular immunofluorescence detection.

In another preferred embodiment, the medicament is used to block the interaction between PD-1 and PD-L1, and/or to block the interaction between PD-1 and PD-L2.

In another preferred embodiment, the tumor includes, but is not limited to, acute myeloid leukemia, chronic myelogenous leukemia, multiple myelopathy, non-Hodgkin's lymphoma, colorectal cancer, breast cancer, colorectal cancer, gastric cancer, liver cancer, leukemia, kidney tumor, lung cancer, small intestine cancer, bone cancer, prostate cancer, prostate cancer, cervical cancer, lymphoma, adrenal tumor, bladder tumor.

In the tenth aspect of the present invention, it provides a pharmaceutical composition comprising: (i) the anti-PD-L2 nanobody of the first aspect of the present invention, the anti-PD-L1 nanobody of the second aspect of the present invention, or the bispecific antibody of the third aspect of the present invention, or the immunoconjugate of the eighth aspect of the present invention; and (ii) a pharmaceutically acceptable carrier.

In another preferred embodiment, the conjugate moiety of the immunoconjugate is a drug, a toxin, and/or a therapeutic isotope.

In another preferred embodiment, the pharmaceutical composition also contains other drugs for treating tumors, such as cytotoxic drugs.

In another preferred embodiment, the other drugs for treating tumors include paclitaxel, doxorubicin, cyclophosphamide, axitinib, lenvatinib, and pimumab.

In another preferred embodiment, the medicament is used to block the interaction between PD-1 and PD-L1, and/or to block the interaction between PD-1 and PD-L2.

In another preferred embodiment, the pharmaceutical composition is used to block PD-1/PD-L1 and/or PD-1/PD-L2 signaling pathways.

In another preferred embodiment, the pharmaceutical composition is used for the treatment of tumors expressing PD-L1 protein (i.e., PD-L1 positive) and/or expressing PD-L2 protein (i.e., PD-L2 positive).

In another preferred embodiment, the pharmaceutical composition is in the form of injection.

In another preferred embodiment, the pharmaceutical composition is used to prepare a drug for preventing and treating tumors.

In the eleventh aspect of the present invention, it provides one or more uses of the anti-PD-L2 nanobody of the first aspect of the present invention, the anti-PD-L1 nanobody of the second aspect of the present invention, or the bispecific antibody of the third aspect of the present invention, which is selected from the group consisting of:

(i) for the detection of human PD-L1 molecules and/or PD-L2 molecules; (ii) for flow cytometry detection; (iii) for cellular immunofluorescence detection; (iv) for treatment of tumors; (v) for diagnosis of tumors; (vi) for blocking the interaction between PD-1 and PD-L1; and/or (vii) for blocking the interaction between PD-L2 and PD-1.

In another preferred embodiment, the tumor is a tumor that expresses PD-L1 protein (i.e., PD-L1 positive) and/or PD-L2 protein (i.e., PD-L2 positive).

In another preferred embodiment, the use is non-diagnostic and non-therapeutic.

In another preferred embodiment, the antibody is an anti-PD-L1 and/or PD-L2 antibody.

In the twelfth aspect of the invention, it provides a recombinant protein having: (i) the anti-PD-L2 nanobody of the first aspect of the present invention, the anti-PD-L1 nanobody of the second aspect of the present invention, or the bispecific antibody of the third aspect of the present invention; and (ii) optional a tag sequence assisting in expression and/or purification.

In another preferred embodiment, the tag sequence comprises a 6His tag, an HA tag and an Fc tag.

In another preferred embodiment, the recombinant protein specifically binds to PD-L1 and/or PD-L2.

In the thirteenth aspect of the present invention, it provides a method for detecting PD-L1 and/or PD-L2 in a sample, which comprises the steps of: (1) contacting the sample with the anti-PD-L2 nanobody of the first aspect of the present invention, the anti-PD-L1 nanobody of the second aspect of the present invention, or the bispecific antibody of the third aspect of the present invention; (2) detecting whether an antigen-antibody complex is formed, wherein the formation of the complex indicates the presence of PD-L1 and/or PD-L2 in the sample.

In the fourteenth aspect of the present invention, it provides a method of treating a disease, which comprises administering to a subject in need thereof the anti-PD-L2 nanobody of the first aspect of the present invention, the anti-PD-L1 nanobody of the second aspect of the present invention, or the bispecific antibody according to the third aspect of the present invention, the immunoconjugate of the eighth aspect of the present invention, or the pharmaceutical composition of the tenth aspect of the present invention.

In another preferred embodiment, the subject comprises a mammal, preferably a human.

In the fifteenth aspect of the present invention, it provides a PD-L1 and/or PD-L2 detection reagent comprising the immunoconjugate of the eighth aspect of the present invention and a detectably acceptable carrier.

In another preferred embodiment, the coupling moiety of the immunoconjugate is a diagnostic isotope.

In another preferred embodiment, the detectably acceptable carrier is a non-toxic, inert, aqueous carrier medium.

In another preferred embodiment, the detection reagent is one or more reagents selected from the group consisting of an isotope tracer, a contrast agent, a flow detection reagent, a cellular immunofluorescence detection reagent, a magnetic nanoparticle and an imaging agent.

In another preferred embodiment, the detection reagent is used for in vivo detection.

In another preferred embodiment, the dosage form of the detection reagent is liquid or powder (e.g., aqua, injection, lyophilized powder, tablet, buccal, inhaler).

In the sixteenth aspect of the present invention, it provides a kit for detecting PD-L1 and/or PD-L2, which comprises the immunoconjugate of the eighth aspect of the present invention or the detection reagent of the fifteenth aspect of the present invention, and the instructions.

In another preferred embodiment, the instructions describe that the kit is used for non-invasively detecting the PD-L1 and/or PD-L2 expression of the subject to be tested.

In another preferred embodiment, the kit is used for the detection of tumors expressing PD-L1 protein (i.e., PD-L1 positive) and/or PD-L2 protein (i.e., PD-L2 positive).

It should be understood that within the scope of the present invention, each technical features of the present invention described above and in the following (as examples) may be combined with each other to form a new or preferred technical solution, which is not listed here due to space limitations.

DESCRIPTION OF DRAWINGS

FIG. 3 shows the binding activity of D-Na-96 humanized antibodies to CHO-hPD-L2 cells.

FIG. 9 shows the blocking effect of anti-PD-L1/PD-L2 bispecific antibodies on the PDL1/PDL2/PD1/luc signaling pathway.

DETAILED DESCRIPTION

Figure 1:
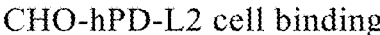
FIG. 1 shows the binding activity of the purified anti-PD-L2 antibodies to CHO-hPD-L2 cells.
Figure 1:
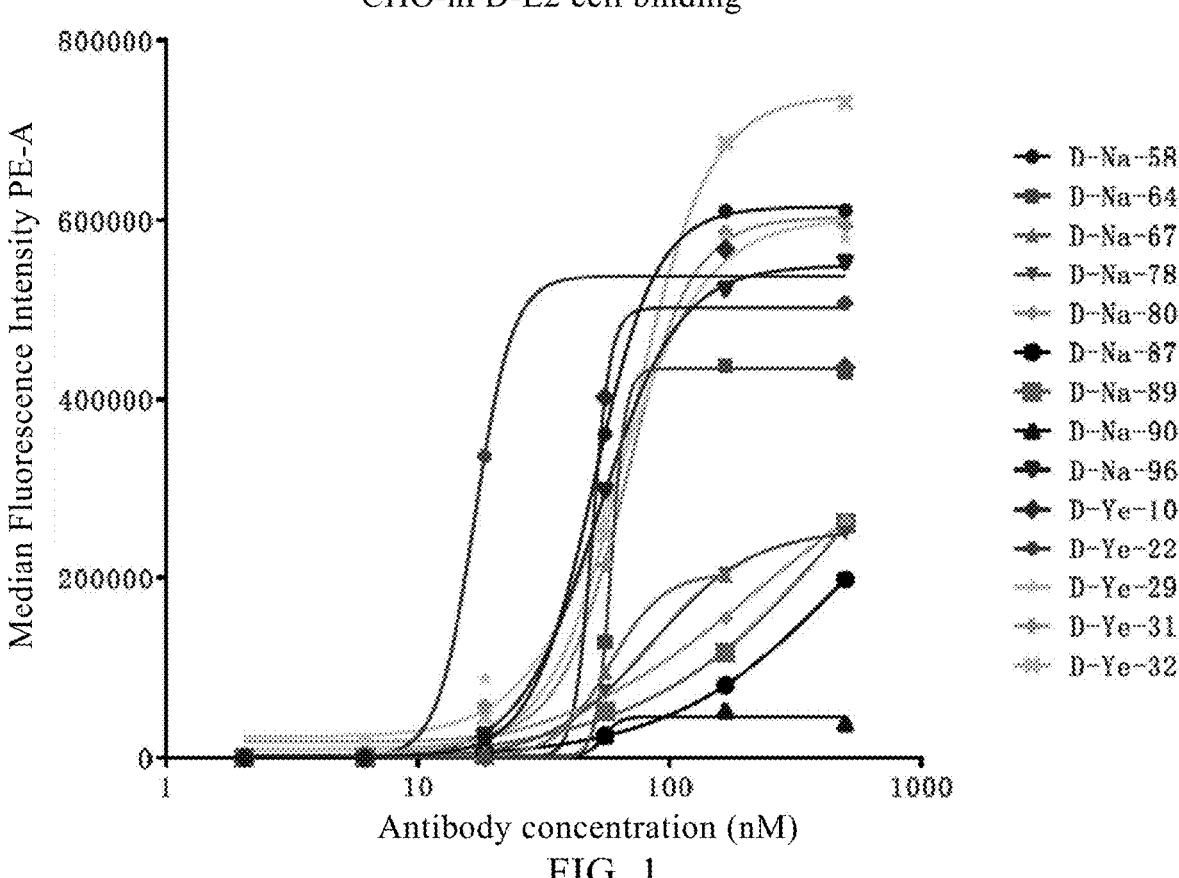

After extensive and in-depth research and a large number of screening, the inventors developed an anti-PD-L1/PD-L2 bispecific antibody for the first time, which comprises an anti-PD-L1 single domain antibody and an anti-PD-L2 single domain antibody. Experiments show that the bispecific antibody of the present invention has good binding activity to both PD-L1 and PD-L2 molecules, and can simultaneously block the interaction between PD-1 and PD-L1 and the interaction between PD-1 and PD-L2. It can also simultaneously block the PD-L1/PD-1 and PD-L2/PD-1 signaling pathways in vitro, and activate the expression of downstream reporter genes, so it has good anti-tumor activity. The present invention has been completed on this basis.

Term

In order to make this disclosure easier to understand, certain terms are first defined. As used in this application, unless expressly stated otherwise herein, each of the following terms shall have the meaning given below. Additional definitions are set forth throughout the application.

Bispecific Antibody

As used herein, the terms "bispecific antibody of the present invention", "bi-antibody of the present invention", and "anti-PD-L1/PD-L2 bispecific antibody" have the same meaning and refer to bispecific antibody that specifically recognizes and binds to PD-L1 and PD-L2.

The present invention provides an anti-PD-L1/PD-L2 bispecific antibody, which comprises: an anti-PD-L1 single-domain antibody and an anti-PD-L2 single-domain antibody.

Preferably, the bispecific antibody of the present invention contains a polypeptide with a structure as shown in Formula I or Formula II, or a polypeptide with a structure as shown in Formula III and Formula IV.

$$A\text{-}L1\text{-}Fc1\text{-}L2\text{-}B \tag{Formula I}$$

$$A\text{-}L3\text{-}B\text{-}L4\text{-}Fc1 \tag{Formula II}$$

$$A\text{-}L5\text{-}Fc2\text{-}L6\text{-}Fc1 \tag{Formula III}$$

$$B\text{-}L7\text{-}Fc2 \tag{Formula IV}$$

wherein,

A and B are each independently an anti-PD-L1 single-domain antibody or an anti-PD-L2 single-domain antibody, and A and B are different antibodies;

L1, L2, L3 and L4 are each independently a peptide bond or a linker element;

both Fc1 and Fc2 are the Fc segment of the antibody, wherein Fc1 is the human IgG domain (preferably the LALA mutant IgG domain), and Fc2 is the CH1+CL domain;

"—" is a peptide bond.

In one embodiment, the bispecific antibody has a polypeptide of the structure as shown in Formula I, and the polypeptide forms a homodimer i through disulfide bonding between Fc1.

In one embodiment, the bispecific antibody has a polypeptide of the structure as shown in Formula II, and the polypeptide forms a homodimer ii through disulfide bonding between Fc1.

In one embodiment, the bispecific antibody has a polypeptide sequence of the structure as shown in Formula III and Formula IV, and the polypeptide of the structure as shown in Formula III and the polypeptide of the structure as shown in Formula IV form a heterodimer a by disulfide bonding between Fc2, and the heterodimer ii forms a homodimer iii by disulfide bonding between Fc1.

As used herein, the terms "single domain antibody", "nanobody VHH", and "nanobody" have the same meaning and refer to cloning the variable region of the heavy chain of the antibody, constructing a nanobody (VHH) composed of only one heavy chain variable region, which is the smallest antigen-binding fragment with complete function. Usually, the antibody with natural deletion of light chain and heavy chain constant region 1(CH1) is obtained first, and then the variable region of the antibody heavy chain is cloned to construct a nanobody (VHH) composed of only one heavy chain variable region.

As used herein, the term "variable" means that certain portion of the variable region in an antibody differs in sequence, which is responsible for the binding and specificity of various specific antibodies to their specific antigen. However, the variability is not distributed evenly throughout the variable regions of an antibody. It is concentrated in three fragments called complementarity determination regions (CDRs) or hypervariable regions in light chain and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partical β-sheet structure. The CDRs in each chain are closely linked together via the FR regions, and together with the CDRs of the other chain, form the antigen binding site of an antibody (see Kabat et al., NIH Publ. No. 91-3242, Volume I, pages 647-669 (1991)). Constant regions are not directly involved in the binding of antibodies to antigen, however, they exhibit different effector functions, such as participating in the antibody-dependent cytotoxicity of antibodies.

As used herein, the term "framework region" (FR) refers to amino acid sequence inserted between CDRs, i.e., those portions of the light and heavy chain variable regions of the immunoglobulins that are relatively conserved among immunoglobulins that differ within a single species. The light chain and heavy chain of immunoglobulin each have four FRs, which are called FR1-L, FR2-L, FR3-L, FR4-L and FR1-H, FR2-H, FR3-H and FR4-H. Accordingly, the light chain variable domain may thus be referred to as (FR1-L)-(CDR1-L)-(FR2-L)-(CDR2-L)-(FR3-L)-(CDR3-L)-(FR4-L) and the heavy chain variable domain may thus be represented as (FR1-H)-(CDR1-H)-(FR2-H)-(CDR2-H)-(FR3-H)-(CDR3-H)-(FR4-H). Preferably, the FR of the present invention is a human antibody FR or a derivative thereof, and the derivative of the human antibody FR is substantially identical to a naturally occurring human antibody FR, that is, the sequence identity reaches 85%, 90%, 95%, 96%, 97%, 98% or 99%.

Knowing the amino acid sequence of the CDR, those skilled in the art can easily determine the framework regions FR1-L, FR2-L, FR3-L, FR4-L and/or FR1-H, FR2-H, FR3-H, FR4-H.

As used herein, the term "human framework region" is a framework region that is substantially identical (about 85% or more, specifically 90%, 95%, 97%, 99% or 100%) to the framework region of a naturally occurring human antibody.

As used herein, the term "affinity" is theoretically defined by an equilibrium association between an intact antibody and an antigen. The affinity of the bispecific antibody of the present invention can be evaluated or determined by KD value (dissociation constant) (or other measurement methods), such as Bio-layer interferometry (BLI), by using FortebioRed96 instrument.

As used herein, the term "linker" refers to one or more amino acid residues inserted into the immunoglobulin domain to provide sufficient mobility for the domains of the light and heavy chains to fold into the exchange dual variable region immunoglobulin.

As known to those skilled in the art, an immunoconjugates and the fusion expression product includes: a drug, a toxin, a cytokine, a radionuclide, an enzyme and other diagnostic or therapeutic molecules that bind to the antibody or fragment thereof of the present invention to form a conjugate. The present invention also includes a cell surface marker or antigen that binds to the PD-L1/PD-L2 bispecific antibody or fragment thereof.

As used herein, the terms "variable region" and "complementarity determining region (CDR)" can be used interchangeably.

In a preferred embodiment of the present invention, the heavy chain variable region of the antibody comprises three complementarity determining regions, CDR1, CDR2, and CDR3.

In a preferred embodiment of the present invention, the heavy chain of the antibody comprises the above-mentioned heavy chain variable region and the heavy chain constant region.

In the present invention, the terms "antibody of the present invention", "protein of the present invention", or "polypeptide of the present invention" may be used interchangeably and refer to a polypeptide that specifically binds to PD-L1 and/or PD-L2 protein, such as a protein or polypeptide having a heavy chain variable region. They can contain or do not contain starting methionine.

The invention also provides other proteins or fusion expression products having the antibody of the present invention. Specifically, the present invention includes any protein or protein conjugate and fusion expression product (i.e., immunoconjugate and fusion expression product) having a heavy chain containing variable regions, as long as the variable region is the same as or has at least 90% homology with the variable regions of the heavy chain of the antibody of the present invention, preferably at least 95% homology.

In general, the antigen binding characteristics of an antibody can be described by three specific regions located in the heavy chain variable region, called the variable region (CDR), which are separated into four frame regions (FR). The amino acid sequence of the four FRs is relatively conservative and does not directly participate in the binding reaction. These CDRs form a circular structure, and the β-sheets formed by the FRs in between are spatially close to each other, and the CDRs on the heavy chain and the CDRs on the corresponding light chain constitute the antigen-binding site of the antibody. It can be determined which amino acids constitute the FR or CDR region by comparing the amino acid sequences of antibodies of the same type.

The variable regions of the heavy chains of the antibody of the present invention are of particular interest because at least part of them involve binding antigens. Therefore, the present invention includes those molecules with a CDR-bearing antibody heavy chain variable region, as long as their CDR has more than 90% (preferably more than 95%, most preferably more than 98%) homology with the CDR identified here.

The present invention includes not only intact antibodies, but also fragments of immunologically active antibodies or fusion proteins formed by antibodies with other sequences. Thus, the present invention also includes fragments, derivatives and analogs of the antibody.

As used herein, the terms "fragment", "derivative" and "analog" refer to a polypeptide that substantially retains the same biological function or activity of the antibody of the present invention. The polypeptide fragment, derivative or analog of the present invention may be (i) a polypeptide with one or more conservative or non-conservative amino acid residues (preferably conservative amino acid residues) substituted, and such substituted amino acid residues may or may not be encoded by the genetic code, or (ii) a polypeptide with a substituent group in one or more amino acid residues, or (iii) a polypeptide formed by fusion of a mature polypeptide with another compound (such as a compound that extends the half-life of the polypeptide, such as polyethylene glycol), or (iv) a polypeptide formed by fusion of an additional amino acid sequence to the polypeptide sequence (such as a leader sequence or secretory sequence or sequence or protein sequence used to purify the polypeptide, or a fusion protein formed with a 6His tag). According to the teachings herein, these fragments, derivatives and analogs are within the scope of well-known to those skilled in the art.

The antibody of the present invention refers to a bispecific antibody with PD-L1 and/or PD-L2 protein binding activity. The term also includes variant forms of polypeptides containing the same CDR regions having the same function as the antibody of the present invention. These variants include (but are not limited to): deletion, insertion and/or substitution of one or more (usually 1-50, preferably 1-30, more preferably 1-20, most preferably 1-10) amino acids, and addition of one or more (usually within 20, preferably within 10, more preferably within 5) amino acids at the C-terminal and/or N-terminal. For example, in the art, substitutions with amino acids of similar properties generally do not alter the function of the protein. For another example, addition of one or more amino acids to the C-terminal and/or N-terminal usually does not alter the function of the protein. The term also includes active fragments and active derivatives of the antibody of the present invention.

The variant forms of the polypeptide include homologous sequences, conservative variants, alleles, natural mutants, induced mutants, proteins encoded by DNA capable of hybridizing with the coding DNA of the antibody of the present invention under high or low tightness conditions, and polypeptides or proteins obtained by using anti-serum against the antibody of the present invention.

The present invention also provides other polypeptides, such as fusion proteins containing single domain antibodies or fragments thereof. In addition to the almost full-length polypeptide, the present invention also includes fragments of the single domain antibody of the present invention. Typically, the fragment has at least about 50 contiguous amino acids, preferably at least about 50 contiguous amino acids, more preferably at least about 80 contiguous amino acids, and most preferably at least about 100 contiguous amino acids of the antibody of the present invention.

In the present invention, "conservative variant of the antibody of the present invention" refers to a polypeptide formed by replacing at most 10, preferably at most 8, more preferably at most 5, and most preferably at most 3 amino acids with amino acids of similar properties as compared with the amino acid sequence of the antibody of the present invention. These conservative variant polypeptides are best produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |

TABLE A-continued

| Initial residue | Representative substitution | Preferred substitution |
|---|---|---|
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above antibody or fragment thereof or fusion protein thereof. The polynucleotide of the present invention may be in the form of DNA or RNA. DNA form includes cDNA, genomic DNA, or synthetic DNA. DNA may be single-stranded or double-stranded. DNA may be a coding strand or a non-coding strand.

The polynucleotide encoding the mature polypeptide of the present invention includes: the coding sequence that encodes only the mature polypeptide; the coding sequence of the mature polypeptide and various additional coding sequences; the coding sequence of the mature polypeptide (and optional additional coding sequence) and the non-coding sequence.

The term "polynucleotide encoding a polypeptide" may be a polynucleotide that includes sequence encoding the polypeptide, or a polynucleotide that also includes additional coding and/or non-coding sequences.

The present invention also relates to a polynucleotide that hybridize to the above-mentioned sequence and have at least 50%, preferably at least 70%, and more preferably at least 80% identity between the two sequences. In particular, the present invention relates to a polynucleotide that is hybridizable to the polynucleotide of the present invention under strict conditions. In the present invention, "strict conditions" refers: (1) hybridization and elution at lower ionic strength and higher temperature, such as 0.2×SSC, 0.1% SDS, 60° C.; or (2) hybridization with denaturing agent, such as 50% (v/v) formamide, 0.1% calf serum/0.1% Ficoll, 42° C., etc.; or (3) hybridization occurs only when the identity between the two sequences is at least 90% or more, more preferably 95% or more. Furthermore, the polypeptide encoded by the hybridizable polynucleotide has the same biological function and activity as the mature polypeptide.

The full-length nucleotide sequence or fragments of the antibody of the present invention may generally be obtained by PCR amplification, recombination or artificial synthesis methods. A feasible method is to synthesize the relevant sequence by artificial synthesis, especially when the fragment length is short. Generally, fragments with a long sequence can be obtained by first synthesizing multiple small fragments followed by ligation. In addition, the coding sequence of the heavy chain and the expression tag (such as 6His) can be fused together to form a fusion protein.

Once the relevant sequence is obtained, the recombination method can be used to obtain the relevant sequence in large quantities. This is usually to clone it into a vector, then transfer it into a cell, and then separate the relevant sequence from the proliferated host cell by conventional methods. The biomolecules (nucleic acids, proteins, etc.) involved in the present invention include biomolecules in isolated form.

At present, the DNA sequence encoding the protein (or its fragment, or its derivative) of the present invention can be obtained completely by chemical synthesis. The DNA sequence can then be introduced into various existing DNA molecules (or, for example, vectors) and cells known in the art. In addition, mutations can be introduced into the protein sequence of the present invention by chemical synthesis.

The present invention also relates to a vector comprising the appropriate DNA sequence as described above and an appropriate promoter or control sequence. These vectors can be used to transform appropriate host cells to enable them to express proteins.

Host cells may be prokaryotic cells, such as bacterial cells; or lower eukaryotic cells, such as yeast cells; or higher eukaryotic cells, such as mammalian cells. Representative examples include: *Escherichia coli, Streptomyces*; bacterial cells of *Salmonella typhimurium*; fungal cells such as yeast; insect cells of *Drosophila* S2 or Sf9; animal cells of CHO, COS7, 293 cells, etc.

Transformation of host cells with recombinant DNA can be carried out using conventional techniques well known to those skilled in the art. When the host is a prokaryotic organism such as *Escherichia coli*, the competent cells capable of absorbing DNA can be harvested after the exponential growth period and treated with $CaCl_2$), the steps used are well known in the art. Another method is to use $MgCl_2$. If necessary, the transformation can also be carried out by electroporation. When the host is eukaryotic, the following DNA transfection methods can be used: calcium phosphate co-precipitation method, conventional mechanical methods such as microinjection, electroporation, liposome packaging, etc.

The obtained transformant can be cultured by conventional methods to express the polypeptide encoded by the gene of the present invention. Depending on the host cell used, the medium used in the culture may be selected from a variety of conventional medium. Culture is carried out under conditions suitable for host cell growth. When the host cells grow to an appropriate cell density, the selected promoter is induced by a suitable method (such as temperature conversion or chemical induction), and the cells are cultured for a period of time.

The recombinant polypeptide in the above method may be expressed in the cell, or on the cell membrane, or secreted outside the cell. If necessary, the recombinant protein can be isolated and purified by various separation methods using its physical, chemical and other properties. These methods are well known to those skilled in the art. Examples of these methods include, but are not limited to, conventional renaturation treatment, treatment with a protein precipitant (salting-out method), centrifugation, osmotic breakage, ultra-treatment, ultra-centrifugation, molecular sieve chromatography (gel filtration), adsorption chromatography, ion exchange chromatography, high performance liquid chromatography (HPLC) and other liquid chromatography techniques and combinations of these methods.

The antibody of the present invention can be used alone, or can be combined or coupled with a detectable label (for diagnostic purposes), a therapeutic agent, a PK (protein kinase) modified moiety, or any combination of these substances.

A detectable marker for diagnostic purposes includes, but is not limited to, a fluorescent or luminescent label, a radioactive label, an MRI (magnetic resonance imaging) or CT (electronic computer tomography) contrast agent, or an enzyme capable of producing a detectable product.

A therapeutic agent that can bind or couple with the antibody of the present invention includes, but is not limited: 1. a radionuclide; 2. a biological toxin; 3. A cytokine such as IL-2, etc.; 4. a gold nanoparticle/nanorod; 5. a viral particle; 6. a liposome; 7. a nanomagnetic particle; 8. a prodrug-activating enzyme (e.g., DT-myoflavase (DTD) or biphenyl hydrolase-like protein (BPHL)); 10. a chemotherapeutic agent (e.g., cisplatin) or a nanoparticle in any form, etc.

Pharmaceutical Composition

The present invention also provides a composition. Preferably, the composition is a pharmaceutical composition comprising the above-mentioned antibody or active fragment thereof or fusion protein thereof, and a pharmaceutically acceptable carrier. Typically, these substances may be formulated in a non-toxic, inert and pharmaceutically acceptable aqueous carrier medium, wherein the pH is typically about 5-8 and preferably about 6-8, although the pH may vary depending on the nature of the substance being formulated and the condition to be treated. The formulated pharmaceutical composition may be administered by conventional routes, including (but not limited to) intratumoral, intraperitoneal, intravenous, or topical administration.

The pharmaceutical composition of the present invention may be directly used to bind PD-L1 and/or PD-L2 protein molecules, and thus can be used to treat tumors. In addition, other therapeutic agents may be used at the same time.

The pharmaceutical composition of the present invention contains a safe and effective amount (e.g., 0.001-99 wt %, preferably 0.01-90 wt %, more preferably 0.1-80 wt %) of the above-mentioned single domain antibody of the present invention (or the conjugate thereof) and a pharmaceutically acceptable carrier or excipient. Such carriers include, but are not limited to, saline, buffer, glucose, water, glycerol, ethanol, and a combination thereof. The pharmaceutical formulation should match the mode of administration. The pharmaceutical composition of the present invention may be prepared in the form of an injection, for example, by conventional methods using normal saline or aqueous solutions containing glucose and other adjuvants. The pharmaceutical composition such as an injection and solution should be manufactured under sterile conditions. The dosage of the active ingredient is a therapeutically effective amount, for example, about 10 µg/kg body weight per day to about 50 mg/kg body weight per day. In addition, the polypeptide of the present invention may also be used with other therapeutic agents.

When a pharmaceutical composition is used, a safe and effective amount of the immune conjugate is administered to a mammal, wherein the safe and effective amount is typically at least about 10 µg/kg body weight, and in most cases no more than about 50 mg/kg body weight, preferably about 10 µg/kg body weight to about 10 mg/kg body weight. Of course, the specific dosage should also consider factors such as the administration route and the patient's health status, which are all within the skill range of a skilled physician.

Labeled Antibody

In a preferred embodiment of the present invention, the antibody carries a detectable label. More preferably, the label is selected from the group consisting of an isotope, a colloidal gold label, a colored label or a fluorescent label.

Colloidal gold labeling may be carried out using methods known to those skilled in the art. In a preferred embodiment of the present invention, the PD-L1/PD-L2 bispecific antibody may be labeled with colloidal gold to obtain a colloidal gold labeled antibody.

Detection Method

The present invention also relates to a method for detecting PD-L1 and/or PD-L2 proteins. The steps of the method are roughly as followed: obtaining a cell and/or tissue sample; dissolving the sample in a medium; and detecting the level of PD-L1 and/or PD-L2 protein in the dissolved sample.

In the detection method of the present invention, the sample used is not particularly limited, and a representative example is a cell-containing sample present in a cell preservation solution.

Kit

The present invention also provides a kit containing the antibody (or fragment thereof) or the detection plate of the present invention. In a preferred embodiment of the present invention, the kit further comprises a container, instructions for use, and a buffer, etc.

The present invention also provides a detection kit for detecting PD-L1 and/or PD-L2 levels, which comprises an antibody that recognizes PD-L1 and/or PD-L2 proteins, a lysis medium for dissolving a sample, a common reagent and buffer required for detection, such as various buffers, detection labels, detection substrates, etc. The detection kit may be an in vitro diagnostic device.

Use

As described above, the single domain antibody of the present invention has a wide range of biological application value and clinical application value, and its application relates to the diagnosis and treatment of diseases involved in PD-L1 and/or PD-L2, basic medical research, biological research and other fields. A preferred application is for clinical diagnosis and targeted therapy for PD-L1 and/or PD-L2, such as tumor therapy.

The main advantages of the present invention include:

(1) The nanobody of the present invention is highly specific to a human PD-L1 protein with a correct spatial structure.

(2) The nanobody of the present invention is highly specific to a human PD-L2 protein with a correct spatial structure.

(3) The nanobody of the present invention has strong affinity.

(4) The production of the nanobody of the present invention is simple and convenient.

(5) The present invention can simultaneously block the interaction between PD-L1/PD-1 and PD-L2/PD-1, relieve immunosuppression, and activate the body's immune system to kill tumors.

The present invention is further explained below in conjunction with specific example. It should be understood that these examples are only for illustrating the present invention and not intend to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions recommended by the manufacturer. Unless otherwise stated, percentages and parts are percentages by weight and parts by weight.

TABLE B

| Summary of the sequence of the present invention | | |
|---|---|---|
| D-Na-58 | Amino acid sequence | SEQ ID NO: 1 |
| | Nucleotide sequence | SEQ ID NO: 31 |
| D-Na-64 | Amino acid sequence | SEQ ID NO: 2 |
| | Nucleotide sequence | SEQ ID NO: 32 |
| D-Na-96 | Amino acid sequence | SEQ ID NO: 3 |
| | Nucleotide sequence | SEQ ID NO: 33 |
| D-Na-67 | Amino acid sequence | SEQ ID NO: 4 |
| | Nucleotide sequence | SEQ ID NO: 34 |
| D-Na-78 | Amino acid sequence | SEQ ID NO: 5 |
| | Nucleotide sequence | SEQ ID NO: 35 |

TABLE B-continued

| Summary of the sequence of the present invention | | |
|---|---|---|
| D-Na-80 | Amino acid sequence | SEQ ID NO: 6 |
| | Nucleotide sequence | SEQ ID NO: 36 |
| D-Na-87 | Amino acid sequence | SEQ ID NO: 7 |
| | Nucleotide sequence | SEQ ID NO: 37 |
| D-Na-89 | Amino acid sequence | SEQ ID NO: 8 |
| | Nucleotide sequence | SEQ ID NO: 38 |
| D-Na-90 | Amino acid sequence | SEQ ID NO: 9 |
| | Nucleotide sequence | SEQ ID NO: 39 |
| D-Ye-10 | Amino acid sequence | SEQ ID NO: 10 |
| | Nucleotide sequence | SEQ ID NO: 40 |
| D-Ye-22 | Amino acid sequence | SEQ ID NO: 11 |
| | Nucleotide sequence | SEQ ID NO: 41 |
| D-Ye-29 | Amino acid sequence | SEQ ID NO: 12 |
| | Nucleotide sequence | SEQ ID NO: 42 |
| D-Ye-31 | Amino acid sequence | SEQ ID NO: 13 |
| | Nucleotide sequence | SEQ ID NO: 43 |
| D-Ye-32 | Amino acid sequence | SEQ ID NO: 14 |
| | Nucleotide sequence | SEQ ID NO: 44 |
| HZ-D-Ye-29-3 | Amino acid sequence | SEQ ID NO: 15 |
| | Nucleotide sequence | SEQ ID NO: 45 |
| HZ-D-Na-96-1 | Amino acid sequence | SEQ ID NO: 16 |
| | Nucleotide sequence | SEQ ID NO: 46 |
| HZ-D-Na-96-2 | Amino acid sequence | SEQ ID NO: 17 |
| | Nucleotide sequence | SEQ ID NO: 47 |
| HZ-D-Na-96-3 | Amino acid sequence | SEQ ID NO: 18 |
| | Nucleotide sequence | SEQ ID NO: 48 |
| K-Yr-13 & 14-02 | Amino acid sequence | SEQ ID NO: 19 |
| | Nucleotide sequence | SEQ ID NO: 49 |
| K-Yr-13 & 14-09 | Amino acid sequence | SEQ ID NO: 20 |
| | Nucleotide sequence | SEQ ID NO: 50 |
| K-Yr-13 & 14-16 | Amino acid sequence | SEQ ID NO: 21 |
| | Nucleotide sequence | SEQ ID NO: 51 |
| HZ-K-Yr-13 & 14-02-3 | Amino acid sequence | SEQ ID NO: 22 |
| | Nucleotide sequence | SEQ ID NO: 52 |
| Bi-201 | Amino acid sequence | SEQ ID NO: 23 |
| | Nucleotide sequence | SEQ ID NO: 53 |
| Bi-202 | Amino acid sequence | SEQ ID NO: 24 |
| | Nucleotide sequence | SEQ ID NO: 54 |
| Bi-203 | Amino acid sequence | SEQ ID NO: 25 |
| | Nucleotide sequence | SEQ ID NO: 55 |
| Bi-204 | Amino acid sequence | SEQ ID NO: 26 |
| | Nucleotide sequence | SEQ ID NO: 56 |
| Linker sequence | Amino acid sequence | SEQ ID NO: 27 |
| Fc | Amino acid sequence | SEQ ID NO: 28 |
| CH1 | Amino acid sequence | SEQ ID NO: 29 |
| CL | Amino acid sequence | SEQ ID NO: 30 |
| Each CDR amino acid sequence of D-Na-96 | CDR1 | SEQ ID NO: 57 |
| | CDR2 | SEQ ID NO: 58 |
| | CDR3 | SEQ ID NO: 59 |
| Each CDR amino acid sequence of D-Ye-29 | CDR1 | SEQ ID NO: 60 |
| | CDR2 | SEQ ID NO: 61 |
| | CDR3 | SEQ ID NO: 62 |
| Each CDR amino acid sequence of K-Yr-13&14-02 | CDR1 | SEQ ID NO: 63 |
| | CDR2 | SEQ ID NO: 64 |
| | CDR3 | SEQ ID NO: 65 |

Example 1: Anti-Human PD-L2 Nanobody 1.1 Construction of Nanobody Library

Animal Immunization 1 mg human PD-L2 antigen (purchased from AcroBiosystems) was mixed with Freund's adjuvant in equal volume to immunize 2 llamas once a week for 4 times to stimulate B cells to express antigen-specific nanobodies. After 4 times of immunization, 50 ml of llama peripheral blood was extracted and lymphocytes were separated by lymphocyte isolation solution. Total RNA was extracted by RNA extraction reagent Trizol (purchased from Invitrogen™). Llama total cDNA was obtained by reverse transcription using a cDNA synthesis kit (purchased from Invitrogen™).

Nanobody Gene Amplification

In the first round of PCR, IgG2 and IgG3 sequences were amplified from cDNA:

TABLE 1

First Round PCR Primers

| Name | Sequence (5'to 3') | SEQ ID NO: |
|------|--------------------|------------|
| Upstream primer | GTCCTGGCTGCTCTTCTACAAGG | 66 |
| Downstream primer | GGTACGTGCTGTTGAACTGTTCC | 67 |

The PCR product was subjected to agarose gel electrophoresis, and the fragment at 750 bp was recovered by cutting the gel for the second round of VHH sequence amplification. The second round of PCR amplification primers are as follows:

TABLE 2

Second Round PCR Primers

| Name | Sequence (5'to 3') | SEQ ID NO: |
|------|--------------------|------------|
| Upstream primer | CTAGTGCGGCCGCcTGGAGACGGTGACCTG GGT | 68 |
| Downstream primer | CGCGGATCCCAGGTGCAGCTGCAGGAGTC TGGRGGAGG | 69 |

Using the second round of PCR products as templates, the third round of PCR was performed to add homologous arms to the VHH gene. The third round of PCR amplification primers are as follows:

TABLE 3

Third Round PCR Primers

| Name | Sequence (5'to 3') | SEQ ID NO: |
|------|--------------------|------------|
| Upstream primer | ATTTTTACTGCTGTTTTAT-TCGCAGCA TCCTCCGCATT-AGCTAAAAGAGAGGCT GAAGCACAGGTGCAGCTGCAG-GAGTCT GGRGGAGG | 70 |
| Downstream primer | AGTTGTCAGTTCCTGTGCCCCCCCTCC TCCCGCGC-CACCTCCGCCCGCACCTCC GCCACCAcTGGA-GACGGTGACCTGGGT | 71 |

The target fragment was recovered using a PCR purification kit (purchased from QIAGEN®).

Library Construction

The linearized yeast display vector and the third round of PCR products were mixed and electrotransformed into *Saccharomyces cerevisiae* (purchased from ATCC®) to construct anti-PD-L2 nanobody libraries from two animals and determine the library capacity. The library capacity is 4.47× $10^7$ and 4.14×$10^7$, respectively.

1.2 Screening of PD-L2 Nanobody

Biotinylated Labeling of Human PD-L2 Protein

Human PD-L2 protein (purchased from AcroBiosystems) was dissolved with an appropriate volume of double distilled water, and the biotin was dissolved and mixed with protein solution according to the product instructions of biotin labeling kit (purchased from Thermo), and incubated at 4° C. for 2 hours. Excess biotin was removed with desalination column (purchased from Thermo). Pretreatment of desalination column and sample collection are carried out with reference to the product instructions steps.

Enrichment of Yeast with Specific Binding to PD-L2 by MACS

The VHH library constructed in Example 1.2 was inoculated into SD-CAA amplification medium (IL SD-CAA amplification medium containing 6.7 g YNB, 5 g tyrosine, 13.62 g $Na_2HPO_4 \cdot 12H_2O$, 7.44 g $NaH_2PO_4$ and 2% glucose), and the number of inoculated yeast cells was >10× library capacity (initial amplification concentration=0.50$OD_{600}$/ml), 30° C., 225 rpm overnight. Yeast cells with 10×library capacity were centrifuged for 3000 rpm×5 min (the following centrifugation operations are the same) to remove the culture medium, yeast cells were resuspended with SD-CAA induction medium, and the initial concentration was adjusted to 0.5$OD_{600}$/ml to induce overnight. The concentration of the induced library was determined. Yeast cells with 10× library capacity were taken and centrifuged to remove the culture medium. The yeast cells were resuspended with 50 ml cleaning solution (PBS+ 0.5% BSA+2 mM EDTA) and centrifuged to remove supernatant. The yeast cells were resuspended with 10 ml of cleaning solution.

Biotin-labeled PD-L2 protein (final concentration 100 mM) was added, and incubated at room temperature for 30 min. The yeast cells were collected by centrifugation, and washed with 50 ml of cleaning solution for 3 times. The yeast cells were resuspended with 5 ml of cleaning solution, and 200 μl of SA magnetic beads (purchased from Miltenyi) were added, and incubated upside down for 10 min. The mixture of yeasts and magnetic beads was washed with cleaning solution for 3 times, and the mixture was added to LS purification column (purchased from Miltenyi). The LS purification column was placed on a magnetic frame, and the non-specifically bound yeast cells were removed by washing with cleaning solution. The purification column was taken out from the magnetic frame and cleaning solution was added to elute the yeasts. The eluted yeasts were centrifuged and transferred to 200 ml SD-CAA amplification medium for amplification.

Obtaining High Affinity Yeast Cells by Flow Cytometry

MACS enriched yeast cells were inoculated into SD-CAA amplification medium with initial amplification concentration=0.5$OD_{600}$/ml. The cells were cultured in shake flask at 30° C., 225 rpm overnight. Yeast cells were resuspended with SD-CAA induction medium (IL SD-CAA induction medium containing 6.7 g YNB, 5 g tyrosine, 13.62 g $Na_2HPO_4 \cdot 12H_2O$, 7.44 g $NaH_2PO_4$ and 2% galactose, 2% raffinose and 0.1% glucose) at an initial concentration of 0.5$OD_{600}$/ml, and induced overnight. 1:200 diluted anti-c-Myc mouse antibody (purchased from Thermo) and 100 nM biotin labeled PD-L2 antigen were added, and incubated at room temperature for 10 min. PBS was added to wash the yeasts for 3 times, 1:500 diluted goat anti-mouse IgG (H+L) Alexa Fluor Plus 488 fluorescent antibody (purchased from Invitrogen™) and streptavidin APC conjugate fluorescent antibody (purchased from Invitrogen™) were added, and incubated at 4° C. for 15 min in the dark. 2 ml of PBS was added to resuspend cells and BD FACSAriall instrument was used for sorting to obtain yeast with high binding ability to PD-L2 antigen.

Extraction of Antibody Gene of PD-L2 Nanobody Candidate Molecules

The yeast solution obtained by MACS and FACS enrichment with high binding ability to PD-L2 antigen was cultured overnight at 30° C. and 225 rpm in SD-CAA amplification medium, and the yeast plasmid was extracted according to the instruction of yeast plasmid extraction kit (purchased from Tiangen®). Plasmids were electrotransformed into Top10 competent cells (purchased from Tiangen®), coated with ampicillin resistant plates, and cultured overnight at 37° C. Monoclon was selected for sequencing to obtain VHH gene sequence.

1.3 Construction, Expression and Purification of Heavy Chain Antibody

Constructing Antibody Gene into pCDNA3.1 Expression Vector

The VHH gene sequence was linked to the human IgG1 (LALA mutation) Fc segment, and was constructed into EcoR I/Not I double enzyme linearized pCDNA3.1 vectors by homologous recombinase (purchased from Vazyme). The process is in accordance with the product instructions. The homologous recombination product was transferred into Top10 competent cells, coated with ampicillin resistant plates, cultured overnight at 37° C. Monoclon was selected for sequencing, and plasmids were extracted.

Cell Transfection and Protein Purification

The extracted plasmids were transferred into Expi-CHO cells by using ExpiCHO™ Expression system kit (purchased from Thermo), and the transfection method is in accordance with the product instructions. After 5 days of cell culture, the supernatant was collected and the target protein was purified by protein A magnetic beads (purchased from Kingsley). The magnetic beads were resuspended (1-4 times the volume of the magnetic beads) with an appropriate volume of binding buffer (PBS+0.1% Tween 20, pH 7.4) and then were added to the sample to be purified, incubated at room temperature for 1 hour with gentle shaking. The sample was placed on a magnetic frame (purchased from Beaver), the supernatant was discarded, and the magnetic beads were washed 3 times with binding buffer. According to the volume of 3-5 times the volume of magnetic beads, elution buffer (0.1M sodium citrate, pH3.2) was added to shake for 5-10 min at room temperature. Then the sample was placed back on the magnetic frame, and the elution buffer was collected, transferred to the collection tube that has been added with neutralization buffer (1M Tris, pH 8.54) and mixed evenly to obtain the target protein.

1.4 Purified Anti-PD-L2 Antibody Binding to Human PD-L2

CHO cells overexpressing human PD-L2 (CHO-hPD-L2 cells) were generated by transfection of the pCHO1.0 vector (purchased from Invitrogen™) cloning human PD-L2 cDNA (purchased from Sino Biological). The expanded CHO-hPD-L2 cells were adjusted to a cell density of 2×10⁶ cells/ml, and were added to 96-well flow plate at 100 μl/well, and centrifuged for later use. The purified PD-L2 antibody was diluted with PBS and diluted 3 times from 1000 nm for 12 points. The diluted samples were added to the 96-well flow plate with cells at 100 μl/well, incubated at 4° C. for 30 min, and washed twice with PBS. Goat F(ab')2 anti-human IgG-Fc (PE) (purchased from Abcam) diluted 100 times with PBS was added at 100 μl/well, incubated at 4° C. for 30 min, and washed twice with PBS. PBS was added at 100 μl/well to resuspend cells, and detection was performed on a CytoFlex (Bechman) flow cytometer and the corresponding MFI was calculated.

In the assay experiment of the above method, the experimental results are shown in FIG. 1. All purified samples and CHO-hPD-L2 cells of the present invention have binding activity.

1.5 Affinity Determination of PD-L2 Antibody

ForteBio affinity determination was carried out according to existing methods (Estep, P et al., High throughput solution-based measurement of antibody-antigen affinity and epitope binning. MAbs, 2013.5(2): p. 270-8). In short, the sensor was equilibrated for 30 min under the line of the analysis buffer, and then the baseline was established after online detection for 60 s. The purified antibody obtained as described above was loaded onto the AhQ sensor online. The sensor was then placed in a 100 nM PD-L2 antigen for 5 min, and then it was transferred to PBS for dissociation for 5 min. Kinetic analysis was performed using a 1:1 binding model.

TABLE 4

| Affinities of candidate molecules | | | |
|---|---|---|---|
| No. | KD(M) | Kon(1/Ms) | Koff(1/s) |
| D-Na-58 | 4.86E-10 | 6.68E+05 | 3.25E-04 |
| D-Na-64 | 5.66E-10 | 6.52E+05 | 3.69E-04 |
| D-Na-67 | 3.58E-09 | 9.33E+04 | 3.34E-04 |
| D-Na-78 | 5.95E-09 | 5.81E+04 | 3.45E-04 |
| D-Na-80 | 3.40E-09 | 1.27E+05 | 4.33E-04 |
| D-Na-87 | 6.55E-10 | 4.40E+05 | 2.88E-04 |
| D-Na-89 | 3.31E-09 | 3.39E+05 | 1.12E-03 |
| D-Na-90 | 3.79E-09 | 4.63E+05 | 1.76E-03 |
| D-Na-96 | 1.27E-09 | 8.62E+05 | 1.10E-03 |
| D-Ye-10 | 5.22E-09 | 2.03E+05 | 1.06E-03 |
| D-Ye-22 | 4.51E-09 | 1.83E+05 | 8.25E-04 |
| D-Ye-29 | 1.93E-09 | 1.95E+05 | 3.76E-04 |
| D-Ye-31 | 5.04E-09 | 1.28E+05 | 6.44E-04 |
| D-Ye-32 | 5.69E-09 | 2.56E+05 | 1.46E-03 |

1.6 Purified Anti-PD-L2 Antibody Blocking the Binding of PD-L2 and PD-1

CHO cells overexpressing human PD-1 (CHO-hPD-1 cells) were generated by transfection of the pCHO1.0 vector (purchased from Invitrogen™) cloning human PD-1 cDNA (purchased from Sino Biological). The expanded CHO-hPD-1 cells were adjusted to a cell density of 2×10⁶ cells/ml, and were added to 96-well flow plate at 100 μl/well, and centrifuged for later use. The purified mutant sample was diluted with PBS and diluted 3 times from 1000 nm for 12 points. The diluted samples were added to the 96-well sample dilution plate at 60 μl/well, and biotinylated human PD-L2 protein (purchased from AcroBiosystems) was added at 60 μl/well with the final concentration of 1 μg/ml, which was incubated with the purified sample at 4° C. for 30 min. The co-incubation sample was added to the above-mentioned 96-well flow plate with cells 100 μl/well, incubated at 4° C. for 30 min, and washed twice with PBS. APC goat anti-mouse IgG (minimum×reactive) antibody diluted 100 times with PBS (purchased from Biolegend®) was added at 100 μl/well, incubated at 4° C. for 30 min, and washed twice with PBS. PBS was added at 100 μl/well to resuspend cells, and detection was performed on a CytoFlex (Bechman) flow cytometer and the corresponding MFI was calculated.

Figure 2:
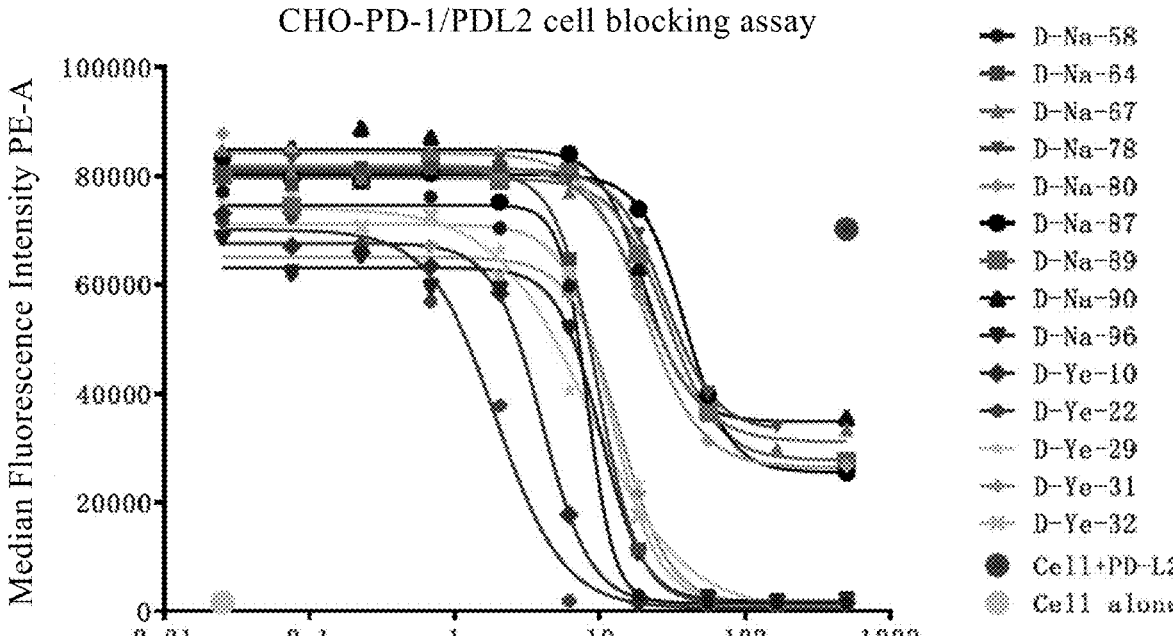
FIG. 2 shows the blocking effect of purified anti-PD-L2 antibodies on the binding of PD-L2 to PD-1.

In the measurement experiment of the above method, the experimental results are shown in FIG. 2. All purified samples of the present invention can block the binding of PD-L2 to PD-1.

1.7 Humanized Construction of PD-L2 Antibody

In order to reduce the immunogenicity of monoclonal antibodies in humans, D-NA-96 and D-Ye-29 antibodies were humanized. The humanization method adopts the VHH humanized universal framework transplantation method, and the method reported in the literature (Vincke, C., et al., General strategy to humanize a camelid single-domain antibody and identification of a universal humanized nanobody scaffold. J Biol Chem 284 (5): 3273-3284) is used to complete the mutation of some amino acids of the antibody framework 2.

This study used IMGT (http://www.imgt.org) to evaluate the humanization level of D-NA-96, D-Ye-29 and humanized sequence, the results are shown in Table 5, the humanization level of all samples after humanization is higher than 80%, which meets the requirements of late-stage drug development.

TABLE 5

Homology of D-NA-96/D-Ye-29 Humanized Sequence and Human

| No. | Germ line | Homology |
| --- | --- | --- |
| D-Na-96 | IGHV3-48 * 03 | 69.40% |
| HZ-D-Na-96-1 | IGHV3-48 * 03 | 84.70% |
| HZ-D-Na-96-2 | IGHV3-48 * 03 | 83.70% |
| HZ-D-Na-96-3 | IGHV3-48 * 03 | 80.60% |
| D-Ye-29 | IGHV3-23 * 01 | 71.1% |
| HZ-D-Ye-29-3 | IGHV3-23 * 01 | 80.40% |

The protein construction, expression and purification methods were the same as in Example 1.3, and HPLC was used to detect the purity of the obtained protein. The HPLC method is as follows, mobile phase: 150 mM $Na_2HPO_4 \cdot 12H_2O$, pH7.0. Chromatographic conditions: detection wavelength: 280 nm, column temperature: 25° C., flow rate: 0.35 ml/min, detection time: 20 min, Zenix-C SEC-300 chromatographic column (SEPAX 4.6×300 mm, 3 μm).

TABLE 6

Purity Test Results of D-Na-96/D-Ye-29 Humanized Antibodies

| No. | Monomer ratio (%) |
| --- | --- |
| D-Na-96 | 100 |
| HZ-D-Na-96-1 | 96.53 |
| HZ-D-Na-96-2 | 99.92 |
| HZ-D-Na-96-3 | 98.84 |
| D-Ye-29 | 100 |
| HZ-D-Ye-29-3 | 98.80 |

1.8 Binding of D-Na-96 Humanized Sample to Human PD-L2

Figure 3:
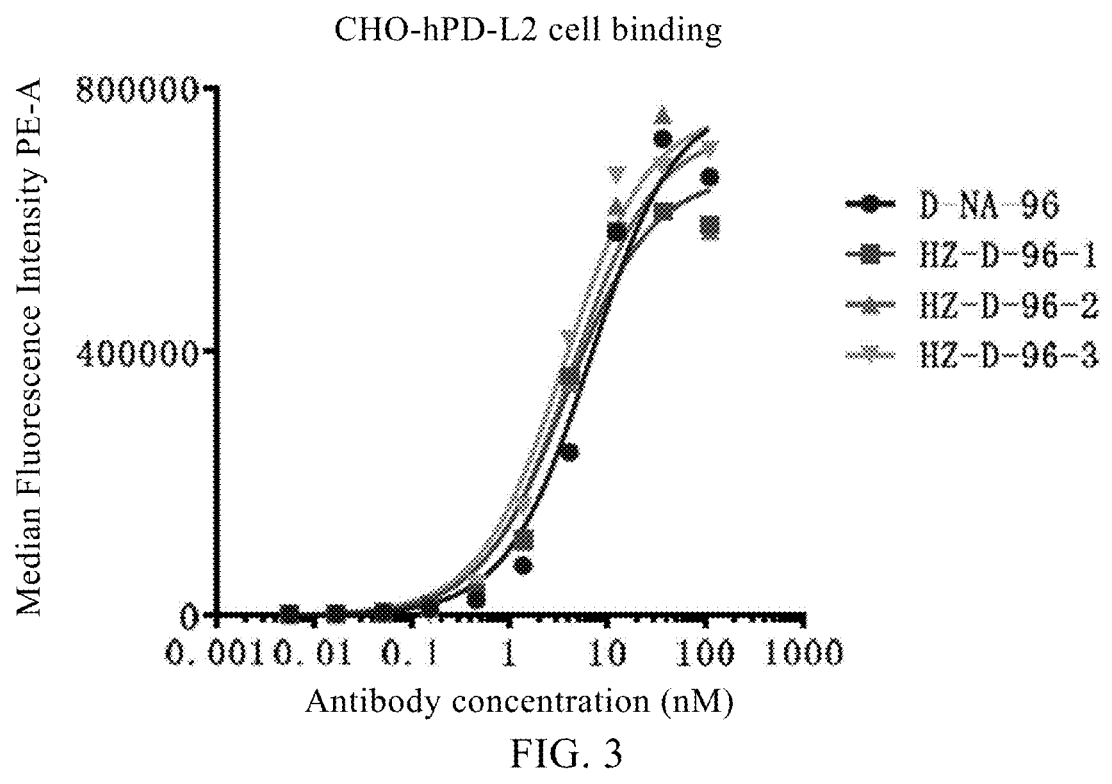

In this experiment, the binding activity of the purified D-Na-96 humanized sample to CHO-hPD-L2 cells was detected. The experimental method was the same as that in Example 1.4. The experimental results are shown in FIG. 3. The sample has good binding activity to CHO-hPD-L2 cells, and the level is comparable to that of D-Na-96.

1.9 Affinity Determination of D-Na-96/D-Ye-29 Humanized Sample

In this experiment, the binding activity of the purified D-Na-96/D-Ye-29 humanized sample to human PD-L2 was detected. The experimental method was the same as that in Example 1.5. The experimental results are shown in Table 7. The D-Na-96/D-Ye-29 humanized sample has good binding activity to human PD-L2.

TABLE 7

Affinities of D-Na-96/D-Ye-29 Humanized Samples

| No. | KD (M) | kon(1/Ms) | kdis(1/s) |
| --- | --- | --- | --- |
| D-Na-96 | 2.50E−09 | 2.62E+05 | 6.55E−04 |
| HZ-D-Na-96-1 | 1.68E−09 | 3.44E+05 | 5.77E−04 |
| HZ-D-Na-96-2 | 1.58E−09 | 3.23E+05 | 5.12E−04 |
| HZ-D-Na-96-3 | 1.99E−09 | 2.97E+05 | 5.90E−04 |
| D-Ye-29 | 1.93E−09 | 1.95E+05 | 3.76E−04 |
| HZ-D-Ye-29-3 | 4.49E−09 | 3.86E+05 | 1.73E−03 |

1.10 D-Na-96 Humanized Sample Blocking the Binding of PD-L2 and PD-1

Figure 4:
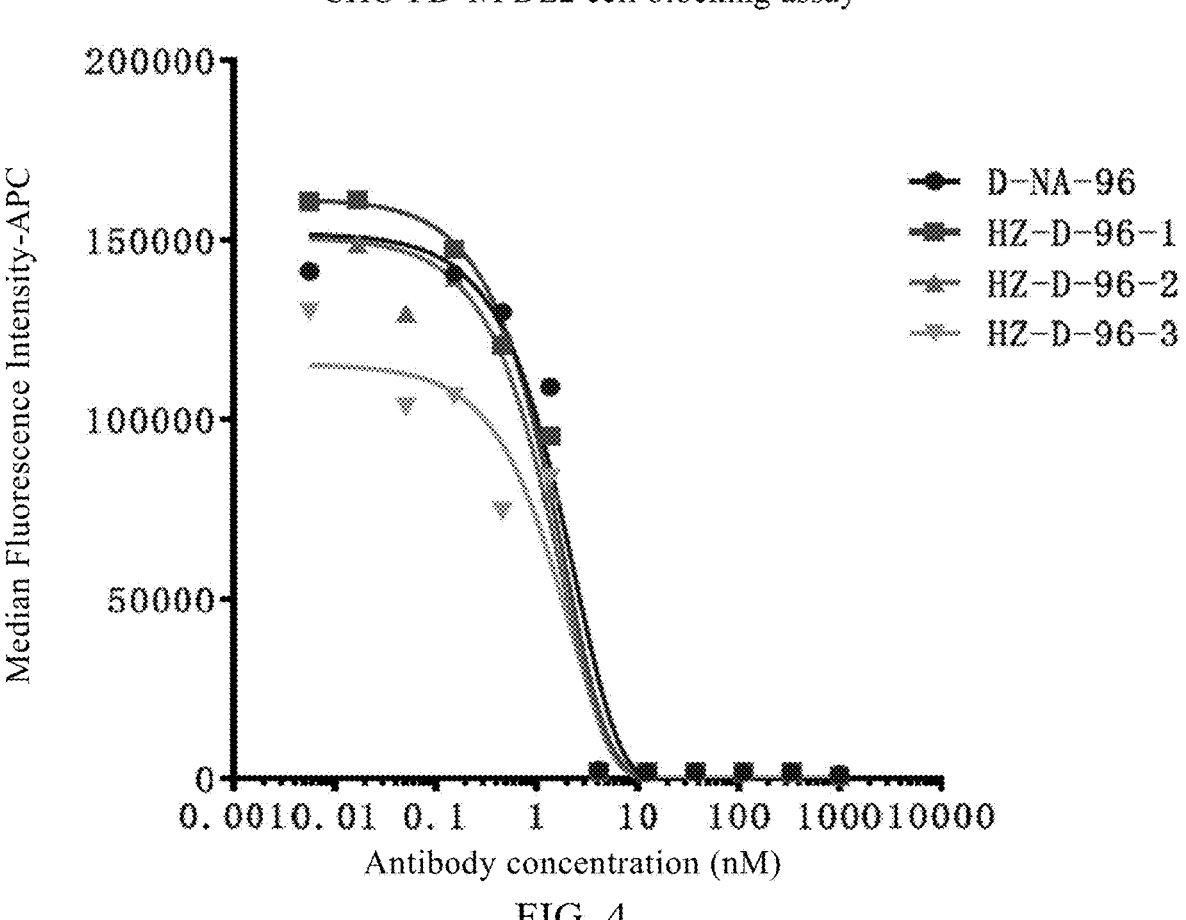
FIG. 4 shows the blocking effect of D-Na-96 humanized antibodies on the binding of PD-L2 to PD-1.

In this experiment, the purified D-Na-96 humanized samples were tested to block the binding of PD-L2 and PD-1. The experimental method was the same as that in Example 1.6. The experimental results are shown in FIG. 4. All the humanized samples of the present invention can block the binding of PD-L2 and PD-1, and the blocking level is comparable to that of D-Na-96.

Example 2: Development of Anti-Human PD-L1 Nanobody

2.1 Construction of Nanobody Library

Animal Immunization 1 mg human PD-L1 antigen (purchased from AcroBiosystems) was mixed with Freund's adjuvant in equal volume to immunize two alpacas (Llama and Alpaca each), and the animals were immunized at weeks 1, 2, 3, 5 and 7 respectively to stimulate B cells to express antigen-specific nanobody. After 5 times of immunization, 300 ml of llama peripheral blood was extracted and lymphocytes were separated by lymphocyte separation. Total RNA was extracted by RNA extraction reagent Trizol (purchased from Invitrogen™). Llama total cDNA was obtained by reverse transcription using a cDNA synthesis kit (purchased from Invitrogen™).

Other nanolibrary construction methods were the same as in Example 1.1.

2.2 Screening of PD-L1 Nanobody and Construction and Expression and Purification of Heavy Chain Antibody In this study, the nanobody sequences that can specifically bind to human PD-L1 were screened from the yeast display library constructed in Example 2.1. The specific screening method was the same as that in Example 1.2. The VHH gene sequence was linked to the human IgG1 (LALA mutation) Fc segment and constructed into the eukaryotic expression vector pCDNA3.1. Heavy chain antibody protein with high purity was prepared by using ExpiCHO expression system and magnetic bead affinity purification system. The method of construction and expression purification of heavy chain antibody pair was the same that in Example 1.3.

2.3 Affinity Determination of PD-L1 Antibody

In this study, the binding activity of the obtained anti-PD-L1 antibody and human PD-L1 protein was detected by ForteBio instrument, and the detection method was the same as that in Example 1.5. The detection results are shown in Table 8. All the three candidate molecules obtained in this study have good binding activity to human PD-L1 protein.

TABLE 8

| Affinities of candidate molecules | | | |
| --- | --- | --- | --- |
| No. | KD(M) | Kon(1/Ms) | Koff(1/s) |
| K-Yr-13 & 14-02 | 9.60E−10 | 5.85E+05 | 5.61E−04 |
| K-Yr-13 & 14-09 | 2.56E−09 | 5.35E+05 | 1.37E−03 |
| K-Yr-13 & 14-16 | 1.10E−08 | 5.53E+05 | 6.06E−03 |
| ATE | | 1.30E−09 | 4.64E+05 | 6.04E−04 |

2.4 Humanized Construction of PD-L1 Antibody

In order to reduce the immunogenicity of monoclonal antibodies in humans, K-Yr-13&14-02 antibody was humanized. The humanization method was the same as in Example 1.7.

This study used IMGT (http://www.imgt.org) to evaluate the humanization level of K-Yr-13&14-02 and humanized sequence, the results are shown in Table 9. The humanization level of all samples after humanization is higher than 80%, which meets the requirements of late-stage drug development.

TABLE 9

| Homology of K-Yr-13&14-02 Humanized Sequence and Human | | |
| --- | --- | --- |
| No. | Germ line | Homology |
| K-Yr-13 & 14-02 | IGHV3-11 * 05 | 74.20% |
| HZ-K-Yr-13 & 14-02-3 | IGHV3-11 * 05 | 80.40% |

Protein construction and expression purification and HPLC purity detection methods are the same as that in Example 1.3. The results are shown in Table 10. After one-step purification, a humanized anti-PD-L1 heavy chain antibody protein with higher purity was obtained.

TABLE 10

| Purity Detection Results of HZ-K-Yr-13 & 14-02-3 | |
| --- | --- |
| No. | Monomer ratio (%) |
| HZ-K-Yr-13 & 14-02-3 | 97.57 |

2.5 Humanized Anti-PD-L1 Nanobody Binding to Human PD-L1

Figures 5, 6:
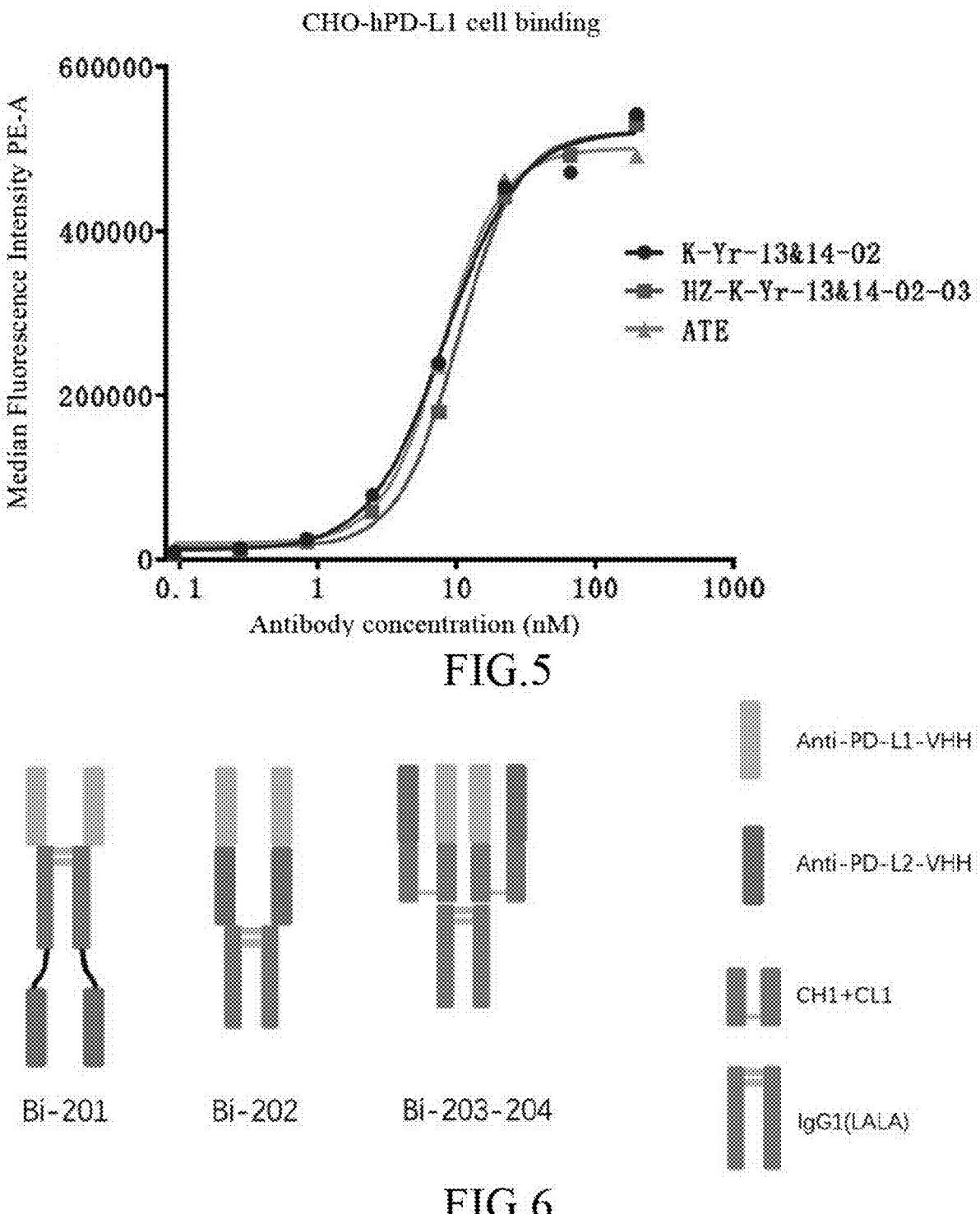
FIG. 5 shows the binding activity of humanized anti-PD-L1 nanobodies to CHO-hPD-L1 cells.
FIG. 6 shows the structure of three different forms of anti-PD-L1/PD-L2 bispecific antibodies.

In this experiment, the binding activity of the purified HZ-K-Yr-13&14-02-3 sample to CHO-hPD-L1 cells was detected. The experimental method was the same as that in Example 1.4. The experimental results are shown in FIG. 5. The HZ-K-Yr-13&14-02-3 has good binding activity to CHO-hPD-L1 cells, and the level is comparable to that of control antibody ATE.

2.6 Affinity Determination of humanized PD-L1 Antibody

In this experiment, the binding activity of the purified HZ-K-Yr-13&14-02-3 to human PD-L1 was detected. The experimental method was the same as that in Example 1.5. The experimental results are shown in Table 11. The HZ-K-Yr-13&14-02-3 has good binding activity to human PD-L2.

TABLE 11

| Humanized sample affinity | | | |
| --- | --- | --- | --- |
| No. | KD (M) | kon(1/Ms) | kdis(1/s) |
| HZ-K-Yr-13 & 14-02-3 | 2.23E−10 | 4.45E+05 | 9.92E−05 |
| ATE | 1.16E−09 | 4.37E+05 | 5.07E−04 |

Example 3 Anti-PD-L1/PD-L2 Bispecific Antibody 3.1 Molecular Construction of Bispecific Antibody Against PD-L1/PD-L2

In this study, three different forms of anti-PD-L1/PD-L2 bispecific antibodies were constructed, and their structural schematic diagram is shown in FIG. 6.

The Bi-201 contains a peptide chain with the amino acid sequence shown in SEQ ID NO: 23, which contains the anti-PD-L1 nanobody HZ-K-Yr-13&14-02-3, and the C-terminal of the nanobody amino acid sequence is directly connected to the human IgG1 (LALA mutant) domain. The anti-PD-L2 nanobody HZ-D-NA-96-1 is connected to the C-terminal of Fc through a flexible peptide chain (GGGGSGGGGSGGGGSGGGGSG)(SEQ ID NO: 27).

The Bi-202 contains a peptide chain with the amino acid sequence shown in SEQ ID NO: 24, and the C-terminal of anti-PD-L1 nanobody HZ-K-13&14-02-3 amino acid sequence is connected to the anti-PD-L2 nanobody HZ-D-NA-96-1 through a flexible peptide chain (GGGGSGGGGSGGGGSGGGGSG) (SEQ ID NO: 27). The C-terminal of the HZ-D-NA-96-1 is directly connected to the human IgG1 (LALA mutant) domain.

Bi-203-204 contains two peptide chains. Peptide chain #1 has the amino acid sequence shown in SEQ ID NO: 25, and the C-terminal of the anti-PD-L1 nanobody HZ-K-Yr-13&14-02-3 amino acid sequence is directly connected to the CH1 amino acid sequence shown in SEQ ID NO: 29 derived from human IgG1; the human IgG1 (LALA mutant) domain is directly connected to the C-terminal of CH1 region thus obtaining the peptide chain #1. Peptide chain #2 has the amino acid sequence shown in SEQ ID NO: 26, which comprises the amino acid sequence shown in SEQ ID NO:16 of the anti-PD-L2 nanobody HZ-D-NA-96-1, and the C-terminal of the nanobody amino acid sequence is directly connected to the human κ light chain constant region (CL) amino acid sequence shown in SEQ ID NO: 30, thereby obtaining the peptide chain #2.

3.2 Expression and Purification of Anti-PD-L1/PD-L2 Bispecific Antibody

In this example, the nucleotide sequences encoding the anti-PD-L1/PD-L2 bispecific antibody Bi-201, Bi-202, and Bi-203-204 constructed in Example 3.1 are all linked to the commercially available eukaryotic expression vector pCDNA 3.1(+) via multi-cloning sites. Heavy chain antibody protein with high purity was prepared by using ExpiCHO expression system and magnetic bead affinity purification system. Protein construction and expression purification and HPLC purity detection methods were the same as that in Example 1.3. The results are shown in Table 12. After one-step purification, the bispecific antibody protein with higher purity was obtained.

27

TABLE 12

Purity Detection Results of Anti-
PD-L1/PD-L2 Bispecific Antibodies

| No. | Monomer ratio (%) |
| --- | --- |
| Bi-201 | 98.26 |
| Bi-202 | 97.67 |
| Bi-203-204 | 99.26 |

3.3 Anti-PD-L1/PD-L2 Bispecific Antibody Affinity Determination

In this study, the binding activity of the obtained anti-PD-L1/PD-L2 bispecific antibody to human PD-L1 or PD-L2 proteins was detected by ForteBio instrument, and the detection method was the same as that in Example 1.5. The detection results are shown in Table 13 and 14. All the three candidate molecules obtained in this study have good binding activity to human PD-L1 and human PD-L2 proteins.

TABLE 13

Affinities of Candidate Molecules to Human PD-L1 Protein

| No. | KD(M) | Kon(1/Ms) | Koff(1/s) |
| --- | --- | --- | --- |
| Bi-201 | 4.81E−10 | 3.34E+05 | 1.61E−04 |
| Bi-202 | 1.66E−09 | 2.07E+05 | 3.43E−04 |
| Bi-203-204 | 1.59E−09 | 2.54E+05 | 4.05E−04 |
| HZ-K-Yr-13 & 14-02-3 | 1.38E−09 | 2.24E+05 | 3.09E−04 |
| ATE | 7.97E−09 | 2.69E+05 | 2.15E−03 |

TABLE 14

Affinities of Candidate Molecules to Human PD-L2 Protein

| No. | KD(M) | Kon(1/Ms) | Koff(1/s) |
| --- | --- | --- | --- |
| Bi-201 | 4.45E−10 | 5.25E+05 | 2.34E−04 |
| Bi-202 | 1.20E−09 | 3.29E+05 | 3.95E−04 |
| Bi-203-204 | 1.14E−09 | 3.72E+05 | 4.24E−04 |
| HZ-D-NA-96-1 | 1.11E−09 | 3.60E+05 | 4.00E−04 |

Figure 7A:
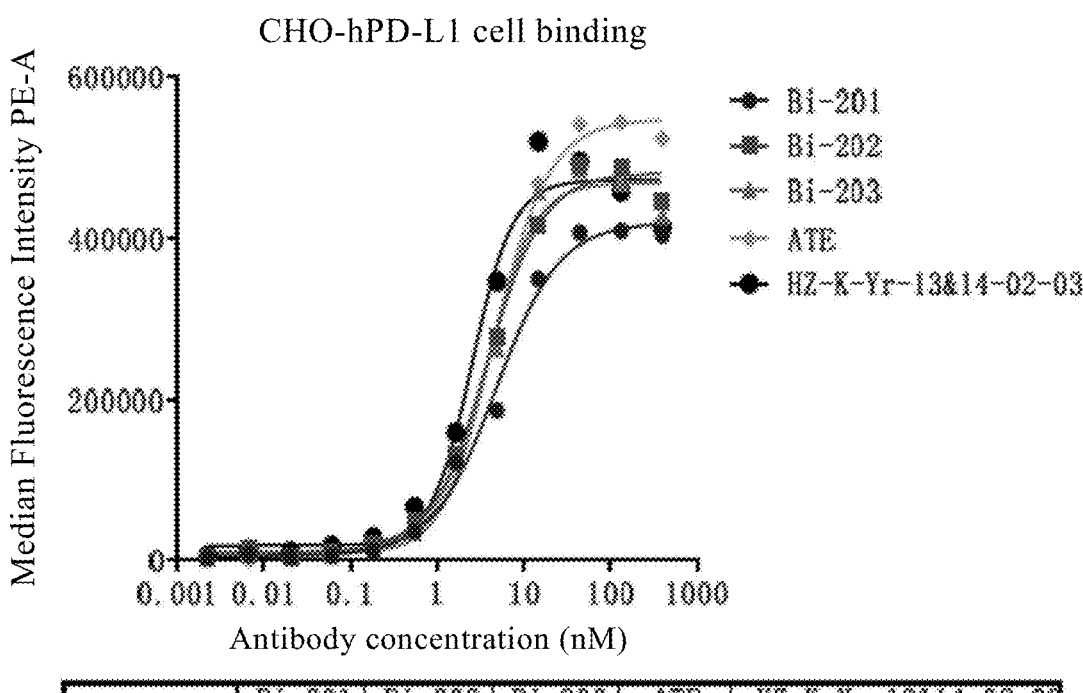
FIGS. 7A and 7B show the binding activity of the anti-PD-L1/PD-L2 bispecific antibodies of the present invention to CHO-hPD-L1 cells (FIG. 7A) or CHO-hPD-L2 cells (FIG. 7B).
Figure 7B:
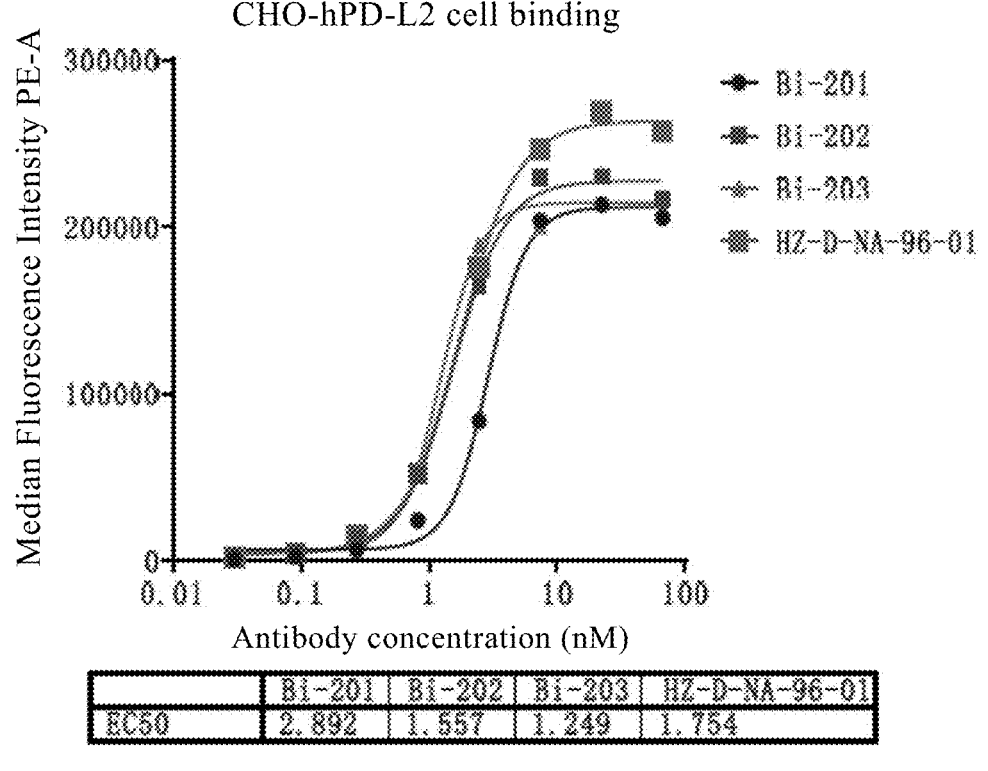

3.4 Binding of Anti-PD-L1/PD-L2 Bispecific Antibody to Human PD-L1 or Human PD-L2 on Cell Surface In this experiment, the binding activity of the anti-PD-L1/PD-L2 bispecific antibody obtained by purification to CHO-hPD-L1 cells or CHO-hPD-L2 was detected. The experimental method was the same as that in Example 1.4, and the experimental results are shown in FIGS. 7A and 7B. Bi-201, Bi-202 and Bi-203-204 have good binding activity to CHO-hPD-L1 cells and CHO-hPD-L2 cells.

3.5 Anti-PD-L1/PD-L2 Bispecific Antibody Blocks PD-L2/PD-L1 Binding to PD-1

The expanded CHO-hPD-1 cells were adjusted to a cell density of $2 \times 10^6$ cells/ml, and were added to 96-well flow plate at 100 μl/well, and centrifuged for later use. The purified mutant sample was diluted with PBS and diluted 3 times from 1000 nm for 12 points. The diluted samples were added to the 96-well sample dilution plate at 60 μl/well, and biotinylated human PD-L2 or PD-L1 protein (purchased from AcroBiosystems) was added at 60 μl/well to the final concentration of 1 μg/ml, and then incubated with the purified sample at 4° C. for 30 min. The co-incubation sample was added to the above-mentioned 96-well flow plate with cells at 100 μl/well, incubated at 4° C. for 30 min, and washed twice with PBS. APC goat anti-mouse IgG (minimum×reactivity) antibody diluted 100 times with PBS (purchased from Biolegend®) was added at 100 μl/well, incubated at 4° C. for 30 min, and washed twice with PBS. PBS was added at 100 μl/well to resuspend cells, and detection was performed on a CytoFlex (Bechman) flow cytometer and the corresponding MFI was calculated.

Figure 8A:
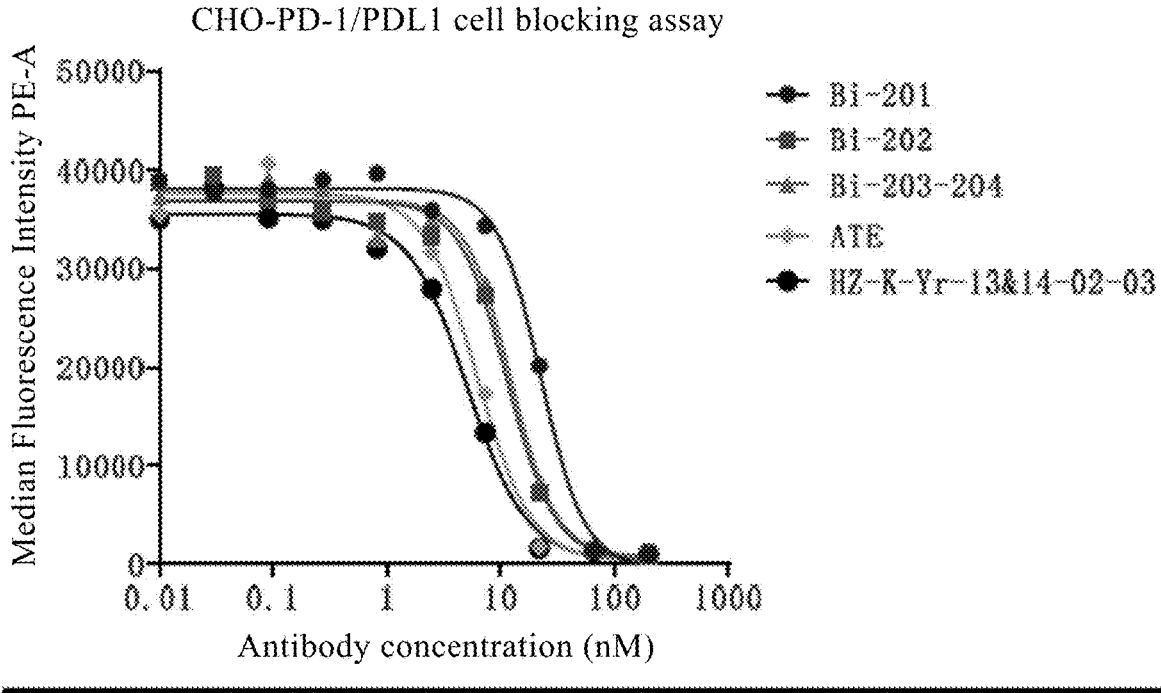
FIGS. 8A and 8B show the blocking effect of the anti-PD-L1/PD-L2 bispecific antibodies of the present invention on the binding of PD-L1 to PD-1 (FIG. 8A) and on the binding of PD-L2 to PD-1 (FIG. 8B).
Figure 8B:
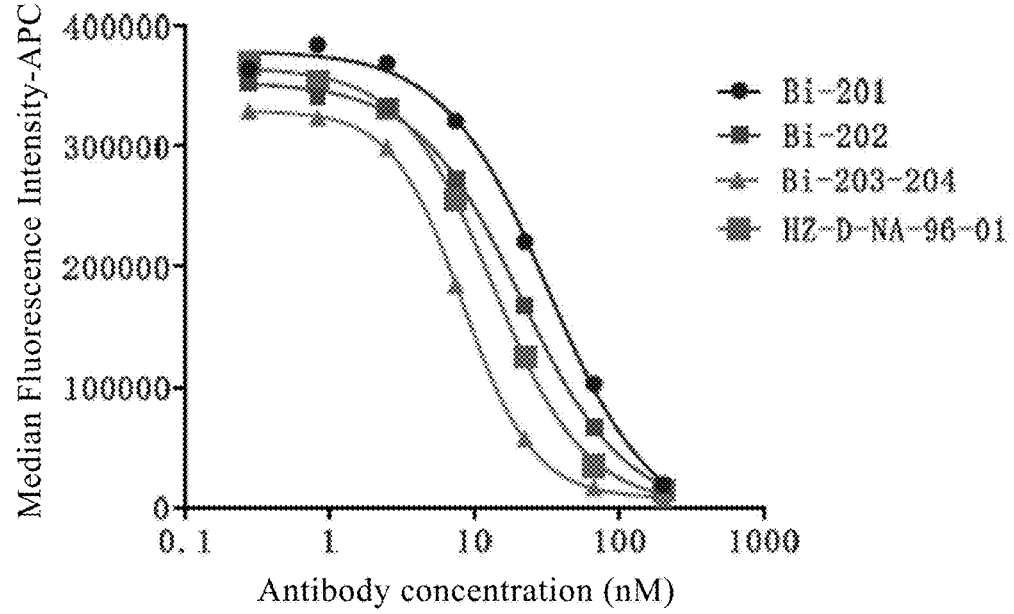

In the measurement experiment of the above method, the experimental results are shown in FIGS. 8A and 8B. All purified samples of the present invention can block the binding of PD-L2 and PD-L1 to PD-1.

3.6 Experiment of Blocking PDL1/PDL2/PD1/Luc Signal Pathway with Anti-PD-L1/PD-L2 Bispecific Antibody PD-L1 and PD-L2 can be co-expressed on tumor cells or immune cells. In this example, the simultaneous blocking effect of purified antibodies Bi-201, Bi-202 and Bi-203-204 on PD-L1/PD-1 pathway and PD-L2/PD-1 pathway was detected by co-incubation of CHO cells expressing human PD-L1 and human PD-L2 (CHO-K1-PD-L1/PD-L2) with Jurkat cells overexpressing human PD-1 and containing NFAT luciferase reporter gene (Jurkat-PD-1-NFAT). The specific methods are as follows.

The CHO-K1-PD-L1/PD-L2 cells were adjusted to a cell density of $5 \times 10^5$ cells/ml and inoculated into 96-well cell culture white plate at 100 μl/well, and was placed at 37° C., 5% $CO_2$ incubator for overnight culture. The purified antibody and the control antibody were gradient diluted with 1640 complete medium for later use. The Jurkat-PD-1-NFAT cells were adjusted to a cell density of $2.5 \times 10^5$ cells/ml with 1640 complete medium to for later use. The white bottom plate was taken out, and the culture supernatant was aspirated. Then the above sample was diluted to the corresponding concentration and added to the white bottom plate at 40 μl/well, and Jurkat-PD-1-NFAT effector cell suspension was simultaneously added at 40 μl/well, and cultured at 37° C., 5% $CO_2$ incubator for 6 hours. Bio-Glo™ reagent (Promega) was added to each well, and the fluorescence signal value was read by using a multifunctional microplate reader.

The experimental results are shown in FIG. 9. The anti-PD-L1/PD-L2 bispecific antibody of the present invention can simultaneously block PD-L1/PD-1 and PD-L2/PD-1 signaling pathways in vitro and activate the expression of downstream reporter genes. However, neither anti-PD-L1 nor anti-PD-L2 monoclonal antibody can completely block the pathway and activate the expression of downstream reporter genes.

All literatures mentioned in the present application are incorporated by reference herein, as though individually incorporated by reference. In addition, it should be understood that after reading the above teaching content of the present invention, various changes or modifications may be made by those skilled in the art, and these equivalents also fall within the scope as defined by the appended claims of the present application.

The invention claimed is:

1. An anti-PD-L2 VHH single domain antibody, wherein the complementarity determining regions (CDRs) of the VHH chain of the anti-PD-L2 VHH single domain antibody are composed of the following:

CDR1 with amino acid sequence as shown in SEQ ID NO: 57; CDR2 with amino acid sequence as shown in SEQ ID NO: 58; and CDR3 with amino acid sequence as shown in SEQ ID NO: 59; or CDR1 with amino acid sequence as shown in SEQ ID NO: 60; CDR2 with amino acid sequence as shown in SEQ ID NO: 61; and CDR3 with amino acid sequence as shown in SEQ ID NO: 62; or, the amino acid sequence of the VHH chain of the anti-PD-L2 VHH single domain antibody is as shown in SEQ ID NO: 1, 2, 4, 5, 6, 7, 8, 9, 10, 11, 13, 14, 17 or 18.

2. An anti-PD-L1 VHH single domain antibody, wherein the complementarity determining regions CDRs of the VHH chain of the anti-PD-L1 VHH single domain antibody are composed of the following:

CDR1 with amino acid sequence as shown in SEQ ID NO: 63; CDR2 with amino acid sequence as shown in SEQ ID NO: 64; and CDR3 with amino acid sequence as shown in SEQ ID NO: 65.

3. A bispecific antibody, which comprises: the anti-PD-L2 VHH single domain antibody of claim 1 and an anti-PD-L1 VHH single domain antibody, wherein the complementarity determining regions CDRs of the VHH chain of the anti-PD-L1 VHH single domain antibody are composed of the following:

CDR1 with amino acid sequence as shown in SEQ ID NO: 63; CDR2 with amino acid sequence as shown in SEQ ID NO: 64; and CDR3 with amino acid sequence as shown in SEQ ID NO: 65.

4. The bispecific antibody of claim 3, wherein the bispecific antibody contains a polypeptide with a structure as shown in Formula I or Formula II, or contains a polypeptide with a structure as shown in Formula III and Formula IV at the same time, $$A\text{-}L1\text{-}Fc1\text{-}L2\text{-}B \qquad \text{(Formula I)}$$

$$A\text{-}L3\text{-}B\text{-}L4\text{-}Fc1 \qquad \text{(Formula II)}$$

$$A\text{-}L5\text{-}Fc2\text{-}L6\text{-}Fc1 \qquad \text{(Formula III)}$$

$$B\text{-}L7\text{-}Fc2 \qquad \text{(Formula IV)}$$

wherein,

A and B are each independently the anti-PD-L1 VHH single domain antibody or the anti-PD-L2 VHH single domain antibody, and A and B are different antibodies;

L1, L2, L3 and L4 are each independently a peptide bond or a linker element;

both Fc1 and Fc2 are the Fc segment of the antibody, wherein Fc1 is the human IgG domain, and Fc2 is the CH1+CL domain;

"—" is a peptide bond.

5. An isolated polynucleotide, wherein the polynucleotide encodes the bispecific antibody of claim 3.

6. A vector comprising the polynucleotide of claim 5.

7. A host cell which comprises the vector of claim 6.

8. A method for producing a bispecific antibody, which comprises the steps:

(a) culturing the host cell of claim 7 under suitable conditions to obtain a culture containing the bispecific antibody; and (b) purifying and/or isolating the culture obtained in step (a) to obtain the bispecific antibody.

9. An immunoconjugate which comprises:

(a) the bispecific antibody of claim 3; and (b) a coupling moiety selected from the group consisting of a detectable label, a drug, a toxin, a cytokine, a radionuclide, or an enzyme, a gold nanoparticle/nanorod, a nanomagnetic particle, a viral coat protein, VLP, and a combination thereof.

10. A pharmaceutical composition which comprises: (i) the bispecific antibody of claim 3, or an immunoconjugate comprising the bispecific antibody; and (ii) a pharmaceutically acceptable carrier.

11. A PD-L1 and/or PD-L2 detection reagent, which comprises the immunoconjugate of claim 9 and a detectably acceptable carrier.

12. A method for detecting PD-L1 and/or PD-L2 in a sample, which comprises the steps of: (1) contacting the sample with the bispecific antibody of claim 3; (2) detecting whether an antigen-antibody complex is formed, wherein the formation of the complex indicates the presence of PD-L1 and/or PD-L2 in the sample.

13. A method of treating a disease, which comprises administering to a subject in need thereof the bispecific antibody of claim 3, or an immunoconjugate comprising the bispecific antibody.

* * * * *

SEQUENCE LISTING

<160> NUMBER OF SEQ ID NOS: 71

<210> SEQ ID NO 1
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-58 VHH chain amino acid sequence

<400> SEQUENCE: 1

```
Gln Val Gln Leu Val Glu Ser Gly Gly Gly Leu Val Gln Ala Gly Gly
1               5                   10                  15

Ser Leu Thr Leu Ser Cys Thr Ala Ser Gly Arg Thr Phe Ser Ser Tyr
            20                  25                  30

Ala Met Ala Trp Phe Arg Gln Ala Pro Gly Lys Glu Arg Glu Leu Leu
        35                  40                  45

Val Thr Ile Ser Arg Ser Gly Ser Thr Thr Tyr Tyr Leu Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Arg Ser Leu Gln Asp Glu Val Tyr Tyr Trp Gly Gln Gly
            100                 105                 110

Thr Gln Val Thr Val Ser Ser
            115
```

<210> SEQ ID NO 2
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-64 VHH chain amino acid sequence

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Met
            20                  25                  30

Thr Ile Gly Trp Phe Arg Gln Thr Pro Gly Lys Glu Arg Glu Phe Val
        35                  40                  45

Ala Gly Ile Gly Trp Ser Thr Ser Lys Thr Val Tyr Lys Asp Ser Val
        50                  55                  60

Lys Gly Arg Phe Thr Ile Ser Thr Asp Asn Ala Lys Lys Thr Val Tyr
65                  70                  75                  80

Leu Gln Met Asn Asn Leu Lys Pro Glu Asp Thr Ala Val Tyr Tyr Cys
                85                  90                  95

Ala Ala Asp Ser Met Asn Arg Gly Gln Phe Asp Tyr Trp Gly Gln Gly
            100                 105                 110

Thr Gln Val Thr Val Ser Ser
            115
```

<210> SEQ ID NO 3
<211> LENGTH: 119

-continued

```
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-96 VHH chain amino acid sequence

<400> SEQUENCE: 3

Gln Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser Ser Met
            20                  25                  30

Thr Ile Gly Trp Phe Arg Gln Thr Pro Gly Lys Glu Arg Glu Phe Val
        35                  40                  45

Ala Gly Ile Gly Trp Thr Ser Gly Leu Thr Val Tyr Ala Asp Ser Val
        50                  55                  60

Lys Gly Arg Phe Thr Ile Ser Arg Asp Asn Ala Glu Lys Thr Met Tyr
65                  70                  75                  80

Leu His Met Asn Asn Leu Lys Pro Glu Asp Thr Ser Val Tyr Tyr Cys
                85                  90                  95

Ala Ala Asp Ser Met Asn Arg Gly Gln Phe Asp Tyr Trp Gly Gln Gly
            100                 105                 110

Thr Gln Val Thr Val Ser Ser
            115

<210> SEQ ID NO 4
<211> LENGTH: 124
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-67 VHH chain amino acid sequence

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Leu Thr Phe Ile Asn
            20                  25                  30

Tyr Ala Met Gly Trp Phe Arg Gln Ala Pro Gly Lys Glu Arg Glu Phe
        35                  40                  45

Val Ala Ala Ile Ser Arg Phe Gly Gly Thr Thr Ser Tyr Ala Asp Ser
        50                  55                  60

Val Lys Asp Arg Phe Ser Ile Thr Arg Asp Val Ala Lys Asp Thr Val
65                  70                  75                  80

Tyr Leu Gln Thr Asn Ser Leu Lys Pro Glu Asp Thr Ala Val Tyr Tyr
                85                  90                  95

Cys Ala Ala Asn Ser Arg Ile Leu Ser Arg Thr Ala Ala Asp Tyr Asp
            100                 105                 110

Tyr Trp Gly Gln Gly Thr Gln Val Thr Val Ser Ser
            115                 120

<210> SEQ ID NO 5
<211> LENGTH: 125
<212> TYPE: PRT
<213> ORGANISM: artificial sequence
<220> FEATURE:
<223> OTHER INFORMATION: synthesized
<220> FEATURE:
```

<221> NAME/KEY: misc_feature
<223> OTHER INFORMATION: D-Na-78 VHH chain amino acid sequence

<400> SEQUENCE: 5

Gln Val Gln Leu Val Glu Ser Gly Gly Gly Leu Val Gln Ala Gly Gly
1               5                   10                  15

Ser Leu Arg Leu Ser Cys Glu Ala Ser Gly Val Ile Ser Ile Asn Tyr
            20                  25                  30

Ala Met Ala Trp Phe Arg Gln Ala Pro Gly Lys Glu Arg Glu Phe Val
            35                  40                  45

Ala Ala Ile Ser Arg Phe Gly Val Thr Thr Ser Tyr Ala Asp Ser Val
        50                  55                  60

Lys Asp Arg Phe Ser Ile Gly Ile Thr Arg Asp Asn Ala Lys Asp Thr
65                  70                  75                  80

Met Tyr Leu Gln Thr Lys Ser Leu Lys Pro Glu Asp Thr Ala Val Tyr
                85                  90                  95

Tyr Cys Ala Ala Asn Ser Arg Ile Leu Ser Arg Thr Ala Lys Asp Tyr
            100                 105                 110

Asp Tyr Trp Gly Gln Gly Thr Gln Val Thr Val Ser Ser
        115                 120                 125

<210> SEQ ID NO 6
<211> LENGTH: 122
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-80 VHH chain amino acid sequence

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Ala Val Ser Gly Val Ser Phe Ile Asn Tyr
            20                  25                  30

Ala Met Gly Trp Phe Arg Gln Ala Pro Gly Lys Glu Arg Glu Phe Val
            35                  40                  45

Ala Ala Ile Ser Arg Phe Gly Gly Thr Thr Ser Tyr Ala Asp Ser Val
        50                  55                  60

Lys Asp Arg Phe Ser Ile Thr Thr Asp Thr Lys Asp Thr Val Tyr Leu
65                  70                  75                  80

Gln Thr Asn Ser Leu Lys Pro Glu Asp Thr Ala Val Tyr Tyr Cys Ala
                85                  90                  95

Ala Asn Ser Arg Ile Leu Ser Arg Thr Ala Lys Asp Tyr Asp Tyr Trp
            100                 105                 110

Gly Gln Gly Thr Gln Val Thr Val Ser Ser
        115                 120

<210> SEQ ID NO 7
<211> LENGTH: 123
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-87 VHH chain amino acid sequence

<400> SEQUENCE: 7

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Ala Tyr
            20                  25                  30

Ala Met Thr Trp Val Arg Gln Ala Pro Gly Lys Gly Leu Glu Phe Leu
            35                  40                  45

Ser Arg Ile Tyr Ser His Gly Ser Lys Ile Ile Tyr Ala Gly Ser Val
        50                  55                  60

Lys Gly Arg Phe Thr Ile Phe Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Pro Asp Asn Ile Pro Thr Thr Gly Glu Lys Tyr Asp Phe
            100                 105                 110

Trp Gly Gln Gly Thr Gln Val Thr Val Ser Ser
        115                 120
```

<210> SEQ ID NO 8
<211> LENGTH: 123
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-89 VHH chain amino acid sequence

<400> SEQUENCE: 8

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ile Asn Tyr
            20                  25                  30

Ala Met Gly Trp Phe Arg Gln Ala Pro Gly Lys Glu Arg Glu Phe Val
            35                  40                  45

Ala Ala Ile Ser Trp Ala Gly Gly Thr Thr Ser Tyr Ala Asp Ser Val
        50                  55                  60

Lys Asp Arg Phe Ser Ile Thr Arg Asp Ser Ala Lys Asp Thr Val Tyr
65                  70                  75                  80

Leu Gln Thr Asn Ser Leu Lys Pro Glu Asp Thr Ala Val Tyr Tyr Cys
                85                  90                  95

Ala Ala Asn Ser Arg Ile Leu Ser Arg Thr Ala Lys Asp Tyr Asp Tyr
            100                 105                 110

Trp Gly Gln Gly Thr Glu Val Thr Val Ser Ser
        115                 120
```

<210> SEQ ID NO 9
<211> LENGTH: 123
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-90 VHH chain amino acid sequence

<400> SEQUENCE: 9

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ile Asn Tyr
            20                  25                  30
```

-continued

```
Ala Met Gly Trp Phe Arg Gln Ala Pro Gly Lys Glu Arg Glu Phe Val
        35                  40                  45

Ala Ala Ile Ser Trp Ala Gly Gly Thr Thr Ser Tyr Ala Asp Ser Val
        50                  55                  60

Lys Asp Arg Phe Ser Ile Thr Arg Asp Ser Ala Lys Asp Thr Val Tyr
65                  70                  75                  80

Leu Gln Thr Asn Ser Leu Lys Pro Glu Asp Thr Ala Val Tyr Tyr Cys
                85                  90                  95

Ala Ala Asn Ser Arg Ile Leu Ser Arg Thr Ala Lys Asp Tyr Asp Tyr
               100                 105                 110

Trp Gly Gln Gly Thr Gln Val Thr Val Ser Ser
        115                 120
```

```
<210> SEQ ID NO 10
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-10 VHH chain amino acid sequence

<400> SEQUENCE: 10
```

```
Gln Val Gln Leu Gln Glu Ser Gly Gly Gly Leu Val Gln Ala Gly Ala
1                   5                  10                  15

Ser Leu Arg Leu Ser Cys Ala Ser Ser Gly Arg Thr Phe Ser Ser Met
                20                  25                  30

Thr Ile Gly Trp Phe Arg Gln Thr Pro Gly Lys Glu Arg Glu Phe Val
        35                  40                  45

Ala Gly Ile Gly Trp Ser Thr Ser Lys Thr Val Tyr Lys Asp Ser Val
        50                  55                  60

Lys Gly Arg Phe Thr Ile Ser Thr Asp Asn Ala Lys Lys Thr Val Tyr
65                  70                  75                  80

Leu Gln Met Asn Asn Leu Lys Pro Glu Asp Thr Ala Val Tyr Tyr Cys
                85                  90                  95

Ala Glu Asp Ser Met Asn Arg Gly Gln Phe Asp Tyr Trp Gly Gln Gly
               100                 105                 110

Thr Gln Val Thr Val Ser Ser
        115
```

```
<210> SEQ ID NO 11
<211> LENGTH: 116
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-22 VHH chain amino acid sequence

<400> SEQUENCE: 11
```

```
Gln Val Gln Leu Gln Glu Ser Gly Gly Gly Leu Val Gln Ala Gly Asp
1                   5                  10                  15

Ser Leu Arg Leu Ser Cys Ile Gly Ser Arg Arg Thr Phe Thr Met Ala
                20                  25                  30

Trp Phe Arg Gln Ala Pro Gly Lys Glu Arg Glu Phe Val Ala Gly Ile
        35                  40                  45

Trp Gly Pro Ala Asp His Thr Ile Tyr Ala Asn Ser Val Lys Gly Arg
```

-continued

```
          50              55              60

Phe Ala Cys Ser Arg Asp Asp Ser Thr Asn Thr Ile Phe Leu Gln Met
65              70              75              80

Asn Ser Leu Glu Leu Glu Asp Thr Ala Leu Tyr Leu Cys Ala Ala Ala
            85              90              95

Asp Ser Ser Gly Asp Asp Phe Glu Tyr Trp Gly Gln Gly Thr Gln Val
            100             105             110

Thr Val Ser Ser
        115

<210> SEQ ID NO 12
<211> LENGTH: 123
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-29 VHH chain amino acid sequence

<400> SEQUENCE: 12

Gln Val Gln Leu Gln Glu Ser Gly Gly Gly Leu Val Gln Pro Gly Gly
1               5               10              15

Ser Leu Arg Leu Ser Cys Ala Ala Ser Gly Ser Glu Phe Ser Phe Ile
            20              25              30

Pro Thr Gly Trp Tyr Arg Gln Thr Pro Gly Lys Gln Arg Asp Leu Val
            35              40              45

Ala Val Phe Thr Ser Gly Gly Leu Thr Asn Tyr Ala Asp Ser Val Lys
        50              55              60

Gly Arg Phe Thr Ile Ser Arg Asn Asn Thr Lys Asn Ile Val Tyr Leu
65              70              75              80

Gln Met Asn Ser Leu Lys Pro Glu Asp Thr Ala Val Tyr Tyr Cys Ser
            85              90              95

Gly Val Pro Gly Pro His Tyr Asn Gly Pro Thr Ser Gly Ile Asn Tyr
            100             105             110

Trp Gly Gln Gly Thr Gln Val Thr Val Ser Ser
        115             120

<210> SEQ ID NO 13
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-31 VHH chain amino acid sequence

<400> SEQUENCE: 13

Gln Val Gln Leu Gln Glu Ser Gly Gly Gly Leu Val Gln Ala Gly Gly
1               5               10              15

Ser Leu Gly Leu Ser Cys Ala Ala Ser Gly Arg Thr Phe Ser Ser Met
            20              25              30

Thr Ile Gly Trp Phe Arg Gln Thr Pro Gly Lys Glu Arg Glu Phe Val
            35              40              45

Ala Gly Ile Gly Trp Ser Thr Ser Lys Thr Val Tyr Lys Asp Ser Val
        50              55              60

Lys Gly Arg Phe Thr Ile Ser Thr Asp Asn Ala Lys Lys Thr Val Tyr
65              70              75              80
```

-continued

```
Leu Gln Met Asn Asn Leu Lys Pro Glu Asp Thr Ala Val Tyr Tyr Cys
                85                  90                  95

Ala Ala Asp Ser Met Asn Arg Gly Gln Phe Asp Tyr Trp Gly Gln Gly
            100                 105                 110

Thr Gln Val Thr Val Ser Ser
        115
```

```
<210> SEQ ID NO 14
<211> LENGTH: 112
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-32 VHH chain amino acid sequence

<400> SEQUENCE: 14
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Val Gly Ser Ile Asn
            20                  25                  30

Ala Met Ala Trp Phe Arg Gln Ala Pro Gly Lys Gln Arg Asp Val Val
        35                  40                  45

Ala His Met Pro Ser Gly Gly Ser Thr His Tyr Ala Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Ala Glu Asp Thr Ala Val Tyr Tyr Cys Trp
                85                  90                  95

Ala Ala Gly Leu Gly Trp Gly Gln Gly Thr Gln Val Thr Val Ser Ser
            100                 105                 110
```

```
<210> SEQ ID NO 15
<211> LENGTH: 123
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Ye-29-3 VHH chain amino acid sequence

<400> SEQUENCE: 15
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Glu Phe Ser Phe Ile
            20                  25                  30

Pro Thr Gly Trp Tyr Arg Gln Ala Pro Gly Lys Gln Arg Glu Leu Val
        35                  40                  45

Ala Val Phe Thr Ser Gly Gly Leu Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ser
                85                  90                  95

Gly Val Pro Gly Pro His Tyr Asn Gly Pro Thr Ser Gly Ile Asn Tyr
            100                 105                 110

Trp Gly Gln Gly Thr Gln Val Thr Val Ser Ser
        115                 120
```

```
<210> SEQ ID NO 16
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-1 VHH chain amino acid sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Met
            20                  25                  30

Thr Ile Gly Trp Phe Arg Gln Ala Pro Gly Lys Gly Leu Glu Phe Val
        35                  40                  45

Ser Gly Ile Gly Trp Thr Ser Gly Leu Thr Val Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Arg Ala Glu Asp Thr Ala Val Tyr Tyr Cys
                85                  90                  95

Ala Ala Asp Ser Met Asn Arg Gly Gln Phe Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-2 VHH chain amino acid sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Met
            20                  25                  30

Thr Ile Gly Trp Phe Arg Gln Ala Pro Gly Lys Gly Leu Glu Phe Val
        35                  40                  45

Ser Gly Ile Gly Trp Thr Ser Gly Leu Thr Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Pro Glu Asp Thr Ala Val Tyr Tyr Cys
                85                  90                  95

Ala Ala Asp Ser Met Asn Arg Gly Gln Phe Asp Tyr Trp Gly Gln Gly
            100                 105                 110

Thr Leu Val Thr Val Ser Ser
        115

<210> SEQ ID NO 18
<211> LENGTH: 119
<212> TYPE: PRT
```

```
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-3 VHH chain amino acid sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Met
            20                  25                  30

Thr Ile Gly Trp Phe Arg Gln Ala Pro Gly Lys Glu Arg Glu Phe Val
        35                  40                  45

Ser Gly Ile Gly Trp Thr Ser Gly Leu Thr Val Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Lys Pro Glu Asp Thr Ala Val Tyr Tyr Cys
                85                  90                  95

Ala Ala Asp Ser Met Asn Arg Gly Gln Phe Asp Tyr Trp Gly Gln Gly
            100                 105                 110

Thr Leu Val Thr Val Ser Ser
        115

<210> SEQ ID NO 19
<211> LENGTH: 124
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-02 VHH chain amino acid sequence

<400> SEQUENCE: 19

Gln Val Gln Leu Val Glu Ser Gly Gly Gly Leu Val Lys Ala Gly Asp
1               5                   10                  15

Ser Leu Arg Leu Ser Cys Ala Ala Ser Gly His Thr Phe Ile Ile Tyr
            20                  25                  30

Ala Ile Gly Trp Phe Arg Gln Ala Pro Gly Lys Glu Arg Glu Phe Val
        35                  40                  45

Ala Thr Ile Asn Trp Ser Gly Ser Met Thr Asn Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Ile Tyr Tyr Cys
                85                  90                  95

Ala Ala Tyr Val Gly Ala Thr Ile Ser Thr Ala His Ser Arg Tyr Asp
            100                 105                 110

Tyr Trp Gly Gln Gly Thr Gln Val Thr Val Ser Ser
        115                 120

<210> SEQ ID NO 20
<211> LENGTH: 124
<212> TYPE: PRT
<213> ORGANISM: artificial sequence
<220> FEATURE:
<223> OTHER INFORMATION: synthesized
<220> FEATURE:
<221> NAME/KEY: misc_feature
```

```
<223> OTHER INFORMATION: K-Yr-13&14-09 VHH chain amino acid sequence

<400> SEQUENCE: 20

Gln Val Gln Leu Val Glu Ser Gly Gly Gly Leu Val Lys Ala Gly Asp
1               5                   10                  15

Ser Leu Arg Leu Ser Cys Ala Ala Ser Gly Arg Thr Phe Thr Ile Tyr
            20                  25                  30

Ala Ile Gly Trp Phe Arg Gln Ala Pro Gly Lys Glu Arg Glu Phe Val
        35                  40                  45

Ala Thr Ile Asn Trp Ser Gly Ser Met Thr Asn Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Ile Tyr Tyr Cys
                85                  90                  95

Ala Ala Tyr Val Gly Ala Thr Ile Ser Thr Ala His Ser Arg Tyr Asp
            100                 105                 110

Tyr Trp Gly Gln Gly Thr Leu Val Thr Val Ser Ala
        115                 120

<210> SEQ ID NO 21
<211> LENGTH: 124
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-16 VHH chain amino acid sequence

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Ala Ser Thr Arg Thr Phe Ile Thr Tyr
            20                  25                  30

Ala Met Gly Trp Phe Arg Gln Ala Pro Gly Lys Glu Arg Glu Phe Val
        35                  40                  45

Ala Ser Ile Asn Trp Ser Gly Ala Ser Thr Tyr Tyr Ala Asp Ser Val
    50                  55                  60

Lys Gly Arg Phe Thr Ile Ser Arg His Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Leu Ser Ala Val Val Val Thr Gln Ile Leu Asp Tyr Asp
            100                 105                 110

Tyr Trp Gly Gln Gly Thr Leu Val Thr Val Ser Ser
        115                 120

<210> SEQ ID NO 22
<211> LENGTH: 124
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-K-Yr-13&14-02-3 VHH chain amino acid
      sequence

<400> SEQUENCE: 22
```

```
Gln Val Gln Leu Val Glu Ser Gly Gly Gly Leu Val Lys Pro Gly Gly
1               5                   10                  15

Ser Leu Arg Leu Ser Cys Ala Ala Ser Gly His Thr Phe Ile Ile Tyr
            20                  25                  30

Ala Ile Gly Trp Phe Arg Gln Ala Pro Gly Lys Gly Leu Glu Phe Val
            35                  40                  45

Ala Thr Ile Asn Trp Ser Gly Ser Met Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Tyr Val Gly Ala Thr Ile Ser Thr Ala His Ser Arg Tyr Asp
            100                 105                 110

Tyr Trp Gly Gln Gly Thr Leu Val Thr Val Ser Ser
            115                 120
```

```
<210> SEQ ID NO 23
<211> LENGTH: 490
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-201 amino acid sequence

<400> SEQUENCE: 23
```

```
Gln Val Gln Leu Val Glu Ser Gly Gly Gly Leu Val Lys Pro Gly Gly
1               5                   10                  15

Ser Leu Arg Leu Ser Cys Ala Ala Ser Gly His Thr Phe Ile Ile Tyr
            20                  25                  30

Ala Ile Gly Trp Phe Arg Gln Ala Pro Gly Lys Gly Leu Glu Phe Val
            35                  40                  45

Ala Thr Ile Asn Trp Ser Gly Ser Met Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Tyr Val Gly Ala Thr Ile Ser Thr Ala His Ser Arg Tyr Asp
            100                 105                 110

Tyr Trp Gly Gln Gly Thr Leu Val Thr Val Ser Ser Asp Lys Thr His
            115                 120                 125

Thr Cys Pro Pro Cys Pro Ala Pro Glu Ala Ala Gly Gly Pro Ser Val
        130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
            165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
            195                 200                 205

Val Leu Thr Val Leu His Gln Asp Trp Leu Asn Gly Lys Glu Tyr Lys
        210                 215                 220
```

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Glu Glu Met Thr Lys Asn Gln Val Ser Leu Thr Cys Leu
                260                 265                 270

Val Lys Gly Phe Tyr Pro Ser Asp Ile Ala Val Glu Trp Glu Ser Asn
                275                 280                 285

Gly Gln Pro Glu Asn Asn Tyr Lys Thr Thr Pro Pro Val Leu Asp Ser
                290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Gly Gly
                340                 345                 350

Gly Gly Ser Gly Gly Gly Gly Ser Gly Gly Gly Gly Ser Gly Gly Gly
                355                 360                 365

Gly Ser Gly Glu Val Gln Leu Val Glu Ser Gly Gly Gly Leu Val Gln
                370                 375                 380

Pro Gly Gly Ser Leu Arg Leu Ser Cys Ala Ala Ser Gly Arg Thr Phe
385                 390                 395                 400

Ser Ser Met Thr Ile Gly Trp Phe Arg Gln Ala Pro Gly Lys Gly Leu
                405                 410                 415

Glu Phe Val Ser Gly Ile Gly Trp Thr Ser Gly Leu Thr Val Tyr Ala
                420                 425                 430

Asp Ser Val Lys Gly Arg Phe Thr Ile Ser Arg Asp Asn Ala Lys Asn
                435                 440                 445

Ser Met Tyr Leu Gln Met Asn Ser Leu Arg Ala Glu Asp Thr Ala Val
                450                 455                 460

Tyr Tyr Cys Ala Ala Asp Ser Met Asn Arg Gly Gln Phe Asp Tyr Trp
465                 470                 475                 480

Gly Gln Gly Thr Leu Val Thr Val Ser Ser
                485                 490

<210> SEQ ID NO 24
<211> LENGTH: 490
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-202 amino acid sequence

<400> SEQUENCE: 24

Gln Val Gln Leu Val Glu Ser Gly Gly Gly Leu Val Lys Pro Gly Gly
1               5                   10                  15

Ser Leu Arg Leu Ser Cys Ala Ala Ser Gly His Thr Phe Ile Ile Tyr
                20                  25                  30

Ala Ile Gly Trp Phe Arg Gln Ala Pro Gly Lys Gly Leu Glu Phe Val
            35                  40                  45

Ala Thr Ile Asn Trp Ser Gly Ser Met Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

-continued

```
Leu Gln Met Asn Ser Leu Lys Pro Asp Asp Thr Ala Val Tyr Tyr Cys
            85              90              95

Ala Ala Tyr Val Gly Ala Thr Ile Ser Thr Ala His Ser Arg Tyr Asp
            100             105             110

Tyr Trp Gly Gln Gly Thr Leu Val Thr Val Ser Ser Gly Gly Gly Gly
        115             120             125

Gly Ser Gly Gly Gly Gly Ser Gly Gly Gly Ser Gly Gly Gly Gly
    130             135             140

Ser Gly Glu Val Gln Leu Val Glu Ser Gly Gly Gly Leu Val Gln Pro
145             150             155             160

Gly Gly Ser Leu Arg Leu Ser Cys Ala Ala Ser Gly Arg Thr Phe Ser
            165             170             175

Ser Met Thr Ile Gly Trp Phe Arg Gln Ala Pro Gly Lys Gly Leu Glu
            180             185             190

Phe Val Ser Gly Ile Gly Trp Thr Ser Gly Leu Thr Val Tyr Ala Asp
            195             200             205

Ser Val Lys Gly Arg Phe Thr Ile Ser Arg Asp Asn Ala Lys Asn Ser
    210             215             220

Met Tyr Leu Gln Met Asn Ser Leu Arg Ala Glu Asp Thr Ala Val Tyr
225             230             235             240

Tyr Cys Ala Ala Asp Ser Met Asn Arg Gly Gln Phe Asp Tyr Trp Gly
            245             250             255

Gln Gly Thr Leu Val Thr Val Ser Ser Asp Lys Thr His Thr Cys Pro
            260             265             270

Pro Cys Pro Ala Pro Glu Ala Ala Gly Gly Pro Ser Val Phe Leu Phe
            275             280             285

Pro Pro Lys Pro Lys Asp Thr Leu Met Ile Ser Arg Thr Pro Glu Val
    290             295             300

Thr Cys Val Val Val Asp Val Ser His Glu Asp Pro Glu Val Lys Phe
305             310             315             320

Asn Trp Tyr Val Asp Gly Val Glu Val His Asn Ala Lys Thr Lys Pro
            325             330             335

Arg Glu Glu Gln Tyr Asn Ser Thr Tyr Arg Val Val Ser Val Leu Thr
            340             345             350

Val Leu His Gln Asp Trp Leu Asn Gly Lys Glu Tyr Lys Cys Lys Val
    355             360             365

Ser Asn Lys Ala Leu Pro Ala Pro Ile Glu Lys Thr Ile Ser Lys Ala
    370             375             380

Lys Gly Gln Pro Arg Glu Pro Gln Val Tyr Thr Leu Pro Pro Ser Arg
385             390             395             400

Glu Glu Met Thr Lys Asn Gln Val Ser Leu Thr Cys Leu Val Lys Gly
            405             410             415

Phe Tyr Pro Ser Asp Ile Ala Val Glu Trp Glu Ser Asn Gly Gln Pro
            420             425             430

Glu Asn Asn Tyr Lys Thr Thr Pro Pro Val Leu Asp Ser Asp Gly Ser
    435             440             445

Phe Phe Leu Tyr Ser Lys Leu Thr Val Asp Lys Ser Arg Trp Gln Gln
    450             455             460

Gly Asn Val Phe Ser Cys Ser Val Met His Glu Ala Leu His Asn His
465             470             475             480

Tyr Thr Gln Lys Ser Leu Ser Leu Ser Pro
            485             490
```

-continued

<210> SEQ ID NO 25
<211> LENGTH: 452
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-203 amino acid sequence

<400> SEQUENCE: 25

Gln Val Gln Leu Val Glu Ser Gly Gly Gly Leu Val Lys Pro Gly Gly
1               5                   10                  15

Ser Leu Arg Leu Ser Cys Ala Ala Ser Gly His Thr Phe Ile Ile Tyr
            20                  25                  30

Ala Ile Gly Trp Phe Arg Gln Ala Pro Gly Lys Gly Leu Glu Phe Val
        35                  40                  45

Ala Thr Ile Asn Trp Ser Gly Ser Met Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Tyr Val Gly Ala Thr Ile Ser Thr Ala His Ser Arg Tyr Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn

-continued

```
            355                 360                 365
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro
    450

<210> SEQ ID NO 26
<211> LENGTH: 226
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-204 amino acid sequence

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Met
                20                  25                  30

Thr Ile Gly Trp Phe Arg Gln Ala Pro Gly Lys Gly Leu Glu Phe Val
            35                  40                  45

Ser Gly Ile Gly Trp Thr Ser Gly Leu Thr Val Tyr Ala Asp Ser Val
    50                  55                  60

Lys Gly Arg Phe Thr Ile Ser Arg Asp Asn Ala Lys Asn Ser Met Tyr
65                  70                  75                  80

Leu Gln Met Asn Ser Leu Arg Ala Glu Asp Thr Ala Val Tyr Tyr Cys
                85                  90                  95

Ala Ala Asp Ser Met Asn Arg Gly Gln Phe Asp Tyr Trp Gly Gln Gly
                100                 105                 110

Thr Leu Val Thr Val Ser Ser Arg Thr Val Ala Ala Pro Ser Val Phe
            115                 120                 125

Ile Phe Pro Pro Ser Asp Glu Gln Leu Lys Ser Gly Thr Ala Ser Val
            130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
                180                 185                 190

Leu Ser Lys Ala Asp Tyr Glu Lys His Lys Val Tyr Ala Cys Glu Val
                195                 200                 205

Thr His Gln Gly Leu Ser Ser Pro Val Thr Lys Ser Phe Asn Arg Gly
            210                 215                 220

Glu Cys
225
```

-continued

<210> SEQ ID NO 27
<211> LENGTH: 21
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: linker

<400> SEQUENCE: 27

Gly Gly Gly Gly Ser Gly Gly Gly Gly Ser Gly Gly Gly Gly Ser Gly
1               5                   10                  15

Gly Gly Gly Ser Gly
            20

<210> SEQ ID NO 28
<211> LENGTH: 225
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: Fc

<400> SEQUENCE: 28

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 29
<211> LENGTH: 103

```
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: CH1

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

```
<210> SEQ ID NO 30
<211> LENGTH: 107
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: CL

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 31
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-58 VHH chain nucleotide sequence

<400> SEQUENCE: 31
caggtgcagc tcgtggagtc aggcggagga ttggtgcagg ctggggggctc tctgacactc      60
```

-continued

```
tcctgtacag cctctggacg caccttcagt agctatgcca tggcctggtt ccgccaggct      120
ccagggaagg agcgtgagtt attagtaact atcagcagga gtggtagtac cacttactat      180
cttgactccg tgaagggccg attcaccatc tccagagaca cgccaagaa cacggtgtat      240 ctgcaaatga acagcctgaa acctgaggac acggccgttt attactgtgc agcaaaaagg      300
tctctccaag acgaagttta ctactggggc caggggaccc aggtcaccgt ctcctca       357
```

```
<210> SEQ ID NO 32
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-64 VHH chain nucleotide sequence

<400> SEQUENCE: 32
```

```
gaggtgcagc tcgtggagtc aggggggaggc ttggtgcagc ctggggggtc tctgagactc       60
tcctgcgcag cctctggacg caccttcagt agcatgacca tcggctggtt ccgccaaact      120
ccagggaagg agcgtgagtt tgtagcaggt attgggtgga gtacgagtaa aacagtctac      180
aaagactccg tgaagggccg attcaccatt tccacagaca atgccaagaa aacggtgtat      240
ctgcaaatga acaacctgaa acctgaggac acggccgttt attactgtgc agcagattca      300
atgaatagag gacagtttga ctactggggc caggggaccc aggtcaccgt ctcctca       357
```

```
<210> SEQ ID NO 33
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-96 VHH chain nucleotide sequence

<400> SEQUENCE: 33
```

```
caggtgcagc tcgtggagtc cggggggagga ttggtgcagg ctggggcctc tctgagactc       60
tcctgcgcag cctctggacg caccttcagt agcatgacca tcggctggtt ccgccaaact      120
ccagggaagg agcgtgagtt tgtagcaggt attgggtgga cgagtggtct cacagtctat      180
gcagactccg tgaagggccg attcaccatt tccagagaca atgccgagaa aacgatgtat      240
ctgcacatga acaatctgaa acctgaggac acgtccgttt attactgtgc agcagattca      300
atgaacagag gacagtttga ctactggggc caggggaccc aggtcaccgt ctcctca       357
```

```
<210> SEQ ID NO 34
<211> LENGTH: 372
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-67 VHH chain nucleotide sequence

<400> SEQUENCE: 34
```

```
caggtgcagc tcgtggagtc tggtggagga ttggtgcagg ctgggggctc tctgagactc       60
tcctgtgcag cctctggtgg actcaccttc attaactatg ccatgggctg gttccgccag      120
gctccaggga aggagcgtga gtttgtagca gctattagtc ggtttggtgg cactacatcc      180
```

-continued

```
tacgcagact ccgtgaagga ccgattcagc atcactagag atgttgccaa agacacggtg          240
tatttgcaaa cgaacagcct gaaacctgag gacacggccg tttattactg tgcagcaaac          300
tcccgtattc tgagtcgaac cgctgcggat tacgattact ggggccaggg gacccaggtc          360
accgtctcct ca                                                             372
```

```
<210> SEQ ID NO 35
<211> LENGTH: 375
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-78 VHH chain nucleotide sequence

<400> SEQUENCE: 35
caggtgcagc tcgtggagtc cggcggagga ttggtgcagg ctgggggctc tctgagactc           60
tcctgtgaag cctctggagt catctccatt aactatgcca tggcctggtt ccgccaggct          120
ccagggaagg agcgtgagtt tgtagctgct attagtcggt ttggtgtaac tacgagttac          180
gcagactccg tgaaggaccg attcagcatc ggcatcacta gagataatgc caaagacaca          240
atgtatctgc aaacgaagag cctgaaacct gaggacacgg ccgtttatta ttgtgcagca          300
aactcccgta ttctgagtcg aaccgctaag gattatgatt actggggcca ggggacccag          360
gtcaccgtct cctca                                                          375
```

```
<210> SEQ ID NO 36
<211> LENGTH: 366
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-80 VHH chain nucleotide sequence

<400> SEQUENCE: 36
gaggtgcagc tcgtggagtc tggtggagga ttggtgcagg ctgggggctc tctgagactc           60
tcctgtgcag tctctggagt ctccttcatt aactatgcca tgggctggtt ccgccaggct          120
ccagggaagg agcgtgagtt tgtagcagct attagtcggt ttggtggcac tacatcctac          180
gcagactccg tgaaggaccg attcagcatc actacagata ccaaagacac ggtgtatctg          240
caaacgaaca gcctgaaacc tgaggacacg gccgtttatt attgtgcagc aaactcccgt          300
attctgagtc gaaccgctaa ggattatgat tactggggcc aggggaccca ggtcaccgtc          360
tcctca                                                                    366
```

```
<210> SEQ ID NO 37
<211> LENGTH: 369
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-87 VHH chain nucleotide sequence

<400> SEQUENCE: 37
caggtgcagc tcgtggagtc tgggggaggc ttggtgcagc ctgggggttc tctgagactc           60
tcctgtgcag cctctggatt cgcttttgat gcctatgcca tgacctgggt ccgacaggct          120
```

```
ccagggaagg gactggagtt tttgtcccgt atttatagtc atggaagtaa gatcatctac      180
gcaggttccg tgaagggccg attcaccatt ttcagagaca acgccaagaa cacggtgtat      240
ctgcaaatga acagcctgaa acctgaggac acggccgtgt attactgtgc agctggtccg      300
gacaacatac cgactacagg tgaaaagtat gacttctggg gtcaggggac ccaggtcacc      360
gtctcctca                                                              369
```

```
<210> SEQ ID NO 38
<211> LENGTH: 369
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-89 VHH chain nucleotide sequence

<400> SEQUENCE: 38
caggtgcagc tcgtggagtc aggggggagga ttggtgcagg ctggggggctc tctgagactc      60 tcctgtgcag cctctggact caccttcatt aactatgcca tgggctggtt ccgccaggct      120
ccagggaagg agcgtgagtt tgtagcagct attagttggg ctggtggcac tacatcctac      180
gcagactccg tgaaggaccg attcagcatc actagagact ctgccaaaga cacggtgtat      240
ctgcaaacga acagcctgaa acctgaggac acggccgttt attattgtgc agcaaactcc      300
cgtattctga gtcgaaccgc taaggattat gattactggg gccagggggac cgaggtcacc      360 gtctcctca                                                              369
```

```
<210> SEQ ID NO 39
<211> LENGTH: 369
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-90 VHH chain nucleotide sequence

<400> SEQUENCE: 39
caggtgcagc tcgtggagtc tgggggagga ttggtgcagg ctggggggctc tctgagactc      60 tcctgtgcag cctctggact caccttcatt aactatgcca tgggctggtt ccgccaggct      120
ccagggaagg agcgtgagtt tgtagcagct attagttggg ctggtggcac tacatcctac      180
gcagactccg tgaaggaccg attcagcatc actagagact ctgccaaaga cacggtgtat      240
ctgcaaacga acagcctgaa acctgaggac acggccgttt attattgtgc agcaaactcc      300
cgtattctga gtcgaaccgc taaggattat gattactggg gccagggggac ccaggtcacc      360 gtctcctca                                                              369
```

```
<210> SEQ ID NO 40
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-10 VHH chain nucleotide sequence

<400> SEQUENCE: 40
caggtgcagc tgcaggagtc tggggggagga ttggtgcagg ctggggggcctc tctgagactc      60
```

-continued

```
tcctgcgcat cctctggacg caccttcagt agcatgacca tcggctggtt ccgccaaact    120
ccagggaagg agcgtgagtt tgtagcaggt attgggtgga gtacgagtaa aacagtctac    180
aaagactccg tgaagggccg attcaccatt tccacagaca atgccaagaa aacggtgtat    240
ctgcaaatga acaacctgaa acctgaggac acggccgttt attactgtgc agaagattca    300
atgaatagag gacagtttga ctactggggc caggggaccc aggtcaccgt ctccagt       357
```

```
<210> SEQ ID NO 41
<211> LENGTH: 348
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-22 VHH chain nucleotide sequence

<400> SEQUENCE: 41
```

```
caggtgcagc tgcaggagtc tggaggagga ttggtgcagg ctggggactc tctgagactc     60
tcctgtatag gttctagacg taccttcacc atggcctggt ccgccaggc tccagggaag    120 gagcgtgaat ttgtggcagg tatttggggt cctgcggatc acacaatcta tgcaaactcc    180
gtgaagggcc gattcgcctg ctccagagac gattccacga atacgatttt tttgcaaatg    240
aacagcctgg aacttgagga cacggccctt tatctctgtg cagcagcgga ctccagtggg    300
gatgactttg agtattgggg ccagggggacc caggtcaccg tctccagt               348
```

```
<210> SEQ ID NO 42
<211> LENGTH: 369
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-29 VHH chain nucleotide sequence

<400> SEQUENCE: 42
```

```
caggtgcagc tgcaggagtc tggggggaggc ttggtgcagc ctggggggtc tctgagactc     60
tcctgtgcag cctctggaag cgagttcagt ttcattccca cgggctggta ccgccagact    120
ccagggaagc agcgcgactt ggtcgcagtt tttacgagtg gcggtctcac aaactatgca    180
gactccgtga agggccgatt caccatctcc agaaacaaca ccaagaacat agtgtatctg    240
caaatgaaca gcctcaaacc tgaggacacg gccgtctatt actgtagtgg agtcccaggt    300
ccacactaca atggtccgac atcggggata aactactggg gccagggggac ccaggtcacc    360 gtctccagt                                                            369
```

```
<210> SEQ ID NO 43
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-31 VHH chain nucleotide sequence

<400> SEQUENCE: 43
```

```
caggtgcagc tgcaggagtc tggaggagga ttggtgcagg ctggggggctc tctgggactc     60 tcctgcgcag cctctggacg caccttcagt agcatgacca tcggctggtt ccgccaaact    120
```

-continued

```
ccagggaagg agcgtgagtt tgtagcaggt attgggtgga gtacgagtaa aacagtctac      180
aaagactccg tgaagggccg attcaccatt tccacagaca atgccaagaa aacggtgtat      240
ctgcaaatga caacctgaa acctgaggac acggccgttt attactgtgc agcagattca      300
atgaatagag gacagtttga ctactggggc caggggaccc aggtcaccgt ctccagt        357
```

```
<210> SEQ ID NO 44
<211> LENGTH: 336
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-32 VHH chain nucleotide sequence

<400> SEQUENCE: 44
```

```
caggtgcagc tgcaggagtc tggaggaggc ttggtgcagg ctggggggtc tctgagactc       60
tcctgtgcag cctctgggag cgtcggcagt atcaatgcca tggcctggtt ccgccaggcg      120
ccagggaagc agcgcgacgt ggtcgcacat atgccttctg tggtagcac acactatgca       180 gactccgtga agggccgatt caccgtctcc agagacaacg ccaagaacac ggtgtatcta      240
caaatgaaca gcctgaaagc tgaggacacg gccgtctatt actgttgggc agctggtctg      300
gggtggggcc aggggaccca ggtcaccgtc tccagt                               336
```

```
<210> SEQ ID NO 45
<211> LENGTH: 369
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Ye-29-3 VHH chain nucleotide sequence

<400> SEQUENCE: 45
```

```
gaggtgcagc tgctggagag cggaggcgga ctggtgcagc ccggaggatc tctgagactg       60
agctgtgctg ctagtgggag cgagttctct tttatcccca caggatggta cagacaggcc      120
cctggaaaac agagagagct ggtggctgtg tttacctctg gagggctgac caactacgcc      180
gactctgtga agggaggtt tactatcagc agggacaaca gcaagaacac agtgtatctc       240
cagatgaaca gtctgagagc cgaagacacc gccgtctatt attgcagcgg cgtgccagga      300
cctcattaca cgggcctac cagcggcatc aactactggg gacagggcac ccaggtgaca      360
gtgtcatcc                                                            369
```

```
<210> SEQ ID NO 46
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-1 VHH chain nucleotide sequence

<400> SEQUENCE: 46
```

```
gaggtgcagc tggtggagag cggaggagga ctggtgcagc ccggcggctc tctgagactg       60
agctgcgccg cctccggaag gacctttagc tccatgacca tcggctggtt cagacaagcc      120
cccggcaagg gactggagtt cgtgagcggc atcggctgga caagcggact gaccgtgtat      180
```

-continued

```
gccgacagcg tcaagggaag gttcaccatc tctagggaca acgccaagaa cagcatgtat    240
ctgcagatga actctctgag ggccgaggac accgccgtgt actactgcgc cgccgacagc    300
atgaacagag gccagttcga ctactggggc caaggcacac tggtgacagt gagcagc       357

<210> SEQ ID NO 47
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-2 VHH chain nucleotide sequence

<400> SEQUENCE: 47
gaggtgcagc tggtggaaag cggcggagga ctggtgcagc ccggcggatc tctgagactc     60
agctgtgctg ccagcggaag gaccttcagc agcatgacca tcggctggtt cagacaagcc    120
cccggcaagg gactggagtt cgtgagcggc atcggctgga caagcggact gaccgtgtat    180
gccgacagcg tcaagggaag gttcaccatc tctagggaca atgccaagaa ctctctgtat    240
ctgcagatga actctctgaa gccccaggat accgccgtgt actactgcgc cgccgatagc    300
atgaataggg gccagttcga ctactggggc caaggcacac tggtgacagt gagcagc       357

<210> SEQ ID NO 48
<211> LENGTH: 357
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-D-Na-96-3 VHH chain nucleotide sequence

<400> SEQUENCE: 48
gaggtgcagc tggtggaaag cggcggagga ctggtgcagc ccggcggatc tctgagactg     60
agctgcgccg ccagcggaag gaccttctcc agcatgacca tcggctggtt taggcaagcc    120
cccggcaagg agagagagtt cgtgagcggc atcggctgga caagcggact gaccgtgtac    180
gccgatagcg tgaagggaag gttcaccatc tctagggaca acgccaagaa ctccatgtat    240
ctgcagatga actctctgaa gccccaggat accgccgtgt actactgcgc cgccgacagc    300
atgaacagag gccagttcga ctactggggc caaggcacac tggtgacagt gtccagc       357

<210> SEQ ID NO 49
<211> LENGTH: 372
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-02 VHH chain nucleotide sequence

<400> SEQUENCE: 49
caagtgcagc tggtagagtc tgggggagga ttggtcaagg ctgggggactc tctgagactc     60 tcctgtgcag cctctggaca caccttcatt atttatgcca ttggctggtt ccgccaggct    120
ccagggaagg agcgtgagtt tgtagcaact attaactgga gtggtagtat gacaaactat    180
acagactccg tgaagggccg attcaccatc tccagagaca cgccaagaa cacggtgtat     240 ctccaaatga acagcctgaa acctgacgac acggccattt attactgtgc ggcttacgtc    300
```

-continued

```
ggtgcgacta tttccaccgc ccattcccga tatgactact ggggccaggg aacccaggtc    360
accgtgtcct ca                                                       372

<210> SEQ ID NO 50
<211> LENGTH: 372
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-09 VHH chain nucleotide sequence

<400> SEQUENCE: 50
caagtgcagc tggtggagtc tggggggagga ttggtcaagg ctgggggactc tctgagactc    60 tcctgtgcag cctctggacg caccttcact atttatgcca ttggctggtt ccgccaggct   120
ccagggaagg agcgtgagtt tgtagcaact attaactgga gtggtagtat gacaaactat   180
acagactccg tgaagggccg attcaccatc tccagagaca acgccaagaa cacggtgtat   240
ctccaaatga acagcctgaa acctgacgac acggccattt attactgtgc ggcttacgtc   300
ggtgcgacta tttccaccgc ccattcccga tatgactact ggggccaggg gaccctggtc   360
actgtctccg ca                                                       372

<210> SEQ ID NO 51
<211> LENGTH: 372
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-16 VHH chain nucleotide sequence

<400> SEQUENCE: 51
gaagtgcagc tggtggagtc tggggggagga ttggtgcagg ctggggggctc tctgagactc    60 tcctgtgcag cctctacacg caccttcatt acctatgcca tgggctggtt ccgccaggct   120
ccagggaagg agcgtgagtt tgtagcatct attaactgga gtggtgctag cacatactat   180
gcagactccg tgaagggccg attcaccatc tccagacaca acgccaagaa cacggtgtat   240
ctgcaaatga acagcctgaa acctgaggac acggccgttt attactgtgc agcagctttg   300
tcagcagtag tagttacaca gatcctagac tatgactact ggggccaggg gaccctggtc   360
accgtctcct ca                                                       372

<210> SEQ ID NO 52
<211> LENGTH: 372
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: HZ-K-Yr-13&14-02-3 VHH chain nucleotide
      sequence

<400> SEQUENCE: 52
caagtgcagc tggtggagag cggaggagga ctggtgaagc ccgcggggctc tctgagactg    60 agctgtgccg cctccggcca caccttcatc atctacgcca tcggctggtt taggcaagcc   120
cccggcaaag gactggagtt cgtggccacc atcaactgga gcggcagcat gaccaactac   180
```

-continued

```
gccgactccg tgaagggaag gttcacaatc tctagggaca acgccaagaa caccgtgtat      240
ctgcagatga actctctgaa gcccgacgac accgccgtgt actactgcgc tgcctatgtg      300
ggcgccacca tcagcacagc ccacagcaga tacgactact ggggacaagg cacactggtg      360
accgtgagca gc                                                          372

<210> SEQ ID NO 53
<211> LENGTH: 1470
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-201 nucleotide sequence

<400> SEQUENCE: 53
caagtgcagc tggtggagag cggaggagga ctggtgaagc ccggcggctc tctgagactg       60
agctgtgccg cctccggcca caccttcatc atctacgcca tcggctggtt taggcaagcc      120
cccggcaaag gactggagtt cgtggccacc atcaactgga gcggcagcat gaccaactac      180
gccgactccg tgaagggaag gttcacaatc tctagggaca acgccaagaa caccgtgtat      240
ctgcagatga actctctgaa gcccgacgac accgccgtgt actactgcgc tgcctatgtg      300
ggcgccacca tcagcacagc ccacagcaga tacgactact ggggacaagg cacactggtg      360
accgtgagca gcgacaaaac ccatacatgt cctccttgcc ccgcccctga ggctgctgga      420
ggccccagcg tgttcctgtt tcccccaag cccaaagata ccctcatgat ctccaggacc       480
cccgaagtga cctgcgtcgt ggtcgacgtg agccacgagg accctgaagt caagttcaac      540
tggtacgtcg atggcgtgga ggtgcacaac gctaagacca accccgggga agagcagtac      600
aattccacct acagggtggt gtccgtcctg acagtgctgc accaagactg gctgaatgga      660
aaggagtaca agtgcaaagt gagcaataag gccctccctg ctcccattga gaagaccatt      720
tccaaggcca aaggccagcc tcgggaaccc caggtgtaca cactgccccc ttccagggag      780
gagatgacca gaaccaggt gagcctcacc tgcctggtga agggcttcta ccctagcgac      840
attgctgtgg agtgggagag caacggccag cccgaaaaca actataagac aacccctccc      900
gtgctggaca gcgacggctc cttctttctg tactccaagc tcaccgtgga caagtccagg      960
tggcaacagg gaaacgtgtt ctcctgctcc gtgatgcacg aggccctcca caaccactac     1020
acccagaaga gcctgagcct gtccctggc ggtggcggcg tagtggcgg aggcgggagt      1080 ggcggtggag ggtcaggtgg tggaggctcg ggtgaggtgc agctggtgga gagcggagga     1140
ggactggtgc agcccggcgg ctctctgaga ctgagctgcg ccgcctccgg aaggaccttt     1200
agctccatga ccatcggctg gttcagacaa gccccccggca agggactgga gttcgtgagc     1260
ggcatcggct ggacaagcgg actgaccgtg tatgccgaca gcgtcaaggg aaggttcacc     1320
atctctaggg acaacgccaa gaacagcatg tatctgcaga tgaactctct gagggccgag     1380
gacaccgccg tgtactactg cgccgccgac agcatgaaca gaggccagtt cgactactgg     1440
ggccaaggca cactggtgac agtgagcagc                                      1470

<210> SEQ ID NO 54
<211> LENGTH: 1470
<212> TYPE: DNA
<213> ORGANISM: artificial sequence
<220> FEATURE:
<223> OTHER INFORMATION: synthesized
<220> FEATURE:
```

-continued

```
<221> NAME/KEY: misc_feature
<223> OTHER INFORMATION: Bi-202 nucleotide sequence

<400> SEQUENCE: 54
caagtgcagc tggtggagag cggaggagga ctggtgaagc ccggcggctc tctgagactg      60
agctgtgccg cctccggcca caccttcatc atctacgcca tcggctggtt taggcaagcc     120
cccggcaaag gactggagtt cgtggccacc atcaactgga gcggcagcat gaccaactac     180
gccgactccg tgaagggaag gttcacaatc tctagggaca cgccaagaa caccgtgtat     240 ctgcagatga actctctgaa gcccgacgac accgccgtgt actactgcgc tgcctatgtg     300
ggcgccacca tcagcacagc ccacagcaga tacgactact ggggacaagg cacactggtg     360
accgtgagca gcggcggtgg cggcggtagt ggcggaggcg ggagtggcgg tggagggtca     420
ggtggtggag gctcgggtga ggtgcagctg gtggagagcg gaggaggact ggtgcagccc     480
ggcggctctc tgagactgag ctgcgccgcc tccggaagga cctttagctc catgaccatc     540
ggctggttca gacaagcccc cggcaaggga ctggagttcg tgagcggcat cggctggaca     600
agcggactga ccgtgtatgc cgacagcgtc aagggaaggt tcaccatctc tagggacaac     660
gccaagaaca gcatgtatct gcagatgaac tctctgaggg ccgaggacac cgccgtgtac     720
tactgcgccg ccgacagcat gaacagaggc cagttcgact actggggcca aggcacactg     780
gtgacagtga gcagcgacaa aacccataca tgtcctcctt gccccgcccc tgaggctgct     840
ggaggcccca gcgtgttcct gtttcccccc aagcccaaag ataccctcat gatctccagg     900 accccccgaag tgacctgcgt cgtggtcgac gtgagccacg aggaccctga agtcaagttc     960
aactggtacg tcgatggcgt ggaggtgcac aacgctaaga ccaaaccccg ggaagagcag    1020
tacaattcca cctacagggt ggtgtccgtc ctgacagtgc tgcaccaaga ctggctgaat    1080
ggaaaggagt acaagtgcaa agtgagcaat aaggccctcc ctgctcccat tgagaagacc    1140
atttccaagg ccaaaggcca gcctcgggaa ccccaggtgt acacactgcc cccttccagg    1200
gaggagatga ccaagaacca ggtgagcctc acctgcctgg tgaagggctt ctaccctagc    1260
gacattgctg tggagtggga gagcaacggc cagcccgaaa acaactataa gacaacccct    1320
cccgtgctgg acagcgacgg ctccttcttt ctgtactcca agctcaccgt ggacaagtcc    1380
aggtggcaac agggaaacgt gttctcctgc tccgtgatgc acgaggccct ccacaaccac    1440
tacacccaga gagcctgag cctgtcccct                                      1470

<210> SEQ ID NO 55
<211> LENGTH: 1356
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-203 nucleotide sequence

<400> SEQUENCE: 55
caagtgcagc tggtggagag cggaggagga ctggtgaagc ccggcggctc tctgagactg      60
agctgtgccg cctccggcca caccttcatc atctacgcca tcggctggtt taggcaagcc     120
cccggcaaag gactggagtt cgtggccacc atcaactgga gcggcagcat gaccaactac     180
gccgactccg tgaagggaag gttcacaatc tctagggaca cgccaagaa caccgtgtat     240 ctgcagatga actctctgaa gcccgacgac accgccgtgt actactgcgc tgcctatgtg     300
ggcgccacca tcagcacagc ccacagcaga tacgactact ggggacaagg cacactggtg     360
```

-continued

```
accgtgagca gcgccagcac aaagggccct tccgtcttcc ctctggcccc ctccagcaag      420
tccacaagcg gaggaaccgc tgccctcggc tgcctcgtga aagactattt ccctgagccc      480
gtgacagtga gctggaatag cggcgctctc acctccggag tccacacctt ccccgctgtg      540
ctgcagagca gcgggactgta tagcctgagc tccgtggtga ccgtgcctag ctcctccctc      600
ggcacccaga cctacatttg caatgtgaac cacaagccta gcaacaccaa ggtggacaag      660
aaggtggagc ccaagagctg cgacaaaacc catacatgtc ctccttgccc cgcccctgag      720
gctgctggag gcccagccgt gttcctgttt ccccccaagc ccaaagatac cctcatgatc      780
tccaggaccc ccgaagtgac ctgcgtcgtg gtcgacgtga gccacgagga ccctgaagtc      840
aagttcaact ggtacgtcga tggcgtggag gtgcacaacg ctaagaccaa accccgggaa      900
gagcagtaca attccaccta cagggtggtg tccgtcctga cagtgctgca ccaagactgg      960
ctgaatggaa aggagtacaa gtgcaaagtg agcaataagg ccctccctgc tcccattgag     1020
aagaccattt ccaaggccaa aggccagcct cgggaacccc aggtgtacac actgccccct     1080
tccagggagg agatgaccaa gaaccaggtg agcctcacct gcctggtgaa gggcttctac     1140
cctagcgaca ttgctgtgga gtgggagagc aacggccagc ccgaaaacaa ctataagaca     1200
acccctcccg tgctggacag cgacggctcc ttctttctgt actccaagct caccgtggac     1260
aagtccaggt ggcaacaggg aaacgtgttc tcctgctccg tgatgcacga ggccctccac     1320
aaccactaca cccagaagag cctgagcctg tcccct                                1356
```

```
<210> SEQ ID NO 56
<211> LENGTH: 678
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: Bi-204 nucleotide sequence

<400> SEQUENCE: 56
gaggtgcagc tggtggagag cggaggagga ctggtgcagc ccggcggctc tctgagactg       60
agctgcgccg cctccggaag gacctttagc tccatgacca tcggctggtt cagacaagcc      120
cccggcaagg gactggagtt cgtgagcggc atcggctgga caagcggact gaccgtgtat      180
gccgacagcg tcaagggaag gttcaccatc tctagggaca cgccaagaa cagcatgtat      240 ctgcagatga actctctgag ggccgaggac accgccgtgt actactgcgc cgccgacagc      300
atgaacagag gccagttcga ctactggggc caaggcacac tggtgacagt gagcagccgg      360
accgtggccg cccctccgt gttcatcttt ccccctccg acgagcagct gaagtccgga      420
accgccagcg tggtgtgcct cctgaacaac ttttacccc gggaggccaa ggtgcagtgg      480
aaggtggaca cgccctgca aagcggcaac tcccaggaat ccgtcaccga gcaggattcc      540
aaggattcca cctacagcct gtcctccacc ctgacactgt ccaaggccga ctacgagaag      600
cacaaggtgt acgcctgcga ggtgacacac caggggcctga gcagcccgt gaccaagtcc      660 ttcaaccggg gcgagtgt                                                       678
```

```
<210> SEQ ID NO 57
<211> LENGTH: 8
<212> TYPE: PRT
<213> ORGANISM: artificial sequence
<220> FEATURE:
<223> OTHER INFORMATION: synthesized
```

-continued

```
<220> FEATURE:
<221> NAME/KEY: misc_feature
<223> OTHER INFORMATION: D-Na-96 CDR1

<400> SEQUENCE: 57

Gly Arg Thr Phe Ser Ser Met Thr
1               5

<210> SEQ ID NO 58
<211> LENGTH: 9
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-96 CDR2

<400> SEQUENCE: 58

Gly Ile Gly Trp Thr Ser Gly Leu Thr
1               5

<210> SEQ ID NO 59
<211> LENGTH: 12
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Na-96 CDR3

<400> SEQUENCE: 59

Ala Ala Asp Ser Met Asn Arg Gly Gln Phe Asp Tyr
1               5                   10

<210> SEQ ID NO 60
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-29 CDR1

<400> SEQUENCE: 60

Gly Ser Glu Phe Ser Phe Ile Pro
1               5

<210> SEQ ID NO 61
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: D-Ye-29 CDR2

<400> SEQUENCE: 61

Val Phe Thr Ser Gly Gly Leu Thr
1               5

<210> SEQ ID NO 62
<211> LENGTH: 17
<212> TYPE: PRT
<213> ORGANISM: artificial sequence
<220> FEATURE:
```

```
<223> OTHER INFORMATION: synthesized
<220> FEATURE:
<221> NAME/KEY: misc_feature
<223> OTHER INFORMATION: D-Ye-29 CDR3

<400> SEQUENCE: 62

Ser Gly Val Pro Gly Pro His Tyr Asn Gly Pro Thr Ser Gly Ile Asn
1               5                   10                  15

Tyr

<210> SEQ ID NO 63
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-02 CDR1

<400> SEQUENCE: 63

Gly His Thr Phe Ile Ile Tyr Ala
1               5

<210> SEQ ID NO 64
<211> LENGTH: 8
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-02 CDR2

<400> SEQUENCE: 64

Ile Asn Trp Ser Gly Ser Met Thr
1               5

<210> SEQ ID NO 65
<211> LENGTH: 17
<212> TYPE: PRT
<213> ORGANISM: artificial sequence
<220> FEATURE:
<223> OTHER INFORMATION: synthesized
<220> FEATURE:
<221> NAME/KEY: misc_feature
<223> OTHER INFORMATION: K-Yr-13&14-02 CDR3

<400> SEQUENCE: 65

Ala Ala Tyr Val Gly Ala Thr Ile Ser Thr Ala His Ser Arg Tyr Asp
1               5                   10                  15

Tyr

<210> SEQ ID NO 66
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 66
gtcctggctg ctcttctaca agg                                              23

<210> SEQ ID NO 67
```

```
<211> LENGTH: 23
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 67
ggtacgtgct gttgaactgt tcc                                              23

<210> SEQ ID NO 68
<211> LENGTH: 33
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 68
ctagtgcggc cgcctggaga cggtgacctg ggt                                  33

<210> SEQ ID NO 69
<211> LENGTH: 38
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 69
cgcggatccc aggtgcagct gcaggagtct ggrggagg                             38

<210> SEQ ID NO 70
<211> LENGTH: 89
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 70
atttttactg ctgttttatt cgcagcatcc tccgcattag ctaaaagaga ggctgaagca    60
caggtgcagc tgcaggagtc tggrggagg                                       89

<210> SEQ ID NO 71
<211> LENGTH: 81
<212> TYPE: DNA
<213> ORGANISM: artificial sequence
<220> FEATURE:
<223> OTHER INFORMATION: synthesized
<220> FEATURE:
<221> NAME/KEY: misc_feature
<223> OTHER INFORMATION: primer

<400> SEQUENCE: 71
agttgtcagt tcctgtgccc cccctcctcc cgcgccacct ccgcccgcac ctccgccacc    60
actggagacg gtgacctggg t                                               81
```